(12) United States Patent
Krappmann et al.

(10) Patent No.: US 9,718,811 B2
(45) Date of Patent: Aug. 1, 2017

(54) (S)-ENANTIOMER OF MEPAZINE

(71) Applicants: Helmholtz Zentrum München—Deutsches Forschungszentrum für Gesundheit und Umwelt (GmbH), Neuherberg (DE); Ludwig-Maximilians-Universität München, Munich (DE)

(72) Inventors: Daniel Krappmann, Munich (DE); Daniel Nagel, Munich (DE); Florian Schlauderer, Inning (DE); Katja Lammens, Gilching (DE); Karl-Peter Hopfner, Berg (DE); Robert A. Chrusciel, Portage, MI (US); Dale L. Kling, Portage, MI (US)

(73) Assignees: Helmholtz Zentrum München—Deutsches Forschungszentrum für Gesundheit und Umwelt (GmbH) (DE); Ludwig-Maximilians—Universität München (DE)

( * ) Notice: Subject to any disclaimer, the term of this patent is extended or adjusted under 35 U.S.C. 154(b) by 0 days.

(21) Appl. No.: 14/900,527

(22) PCT Filed: Jun. 25, 2014

(86) PCT No.: PCT/EP2014/063446
§ 371 (c)(1),
(2) Date: Dec. 21, 2015

(87) PCT Pub. No.: WO2014/207067
PCT Pub. Date: Dec. 31, 2014

(65) Prior Publication Data
US 2016/0137635 A1  May 19, 2016

(30) Foreign Application Priority Data

Jun. 26, 2013 (EP) .................................... 13003260

(51) Int. Cl.
C07D 417/06 (2006.01)
C07D 211/22 (2006.01)

(52) U.S. Cl.
CPC .......... *C07D 417/06* (2013.01); *C07D 211/22* (2013.01)

(58) Field of Classification Search
CPC ..................................................... C07D 417/06
See application file for complete search history.

(56) References Cited

FOREIGN PATENT DOCUMENTS

WO  WO-2007/058850 A2  5/2007
WO  WO-2013/017637 A1  2/2013

OTHER PUBLICATIONS

Nagel et al. Cancer Cell, 2012, vol. 22, pp. 825-837.*
Chhabra et al. Int. J. Appl. Basic Med. Res., 2013, vol. 3, No. 1, pp. 16-18.*
International Search Report for PCT/EP2014/063446, 4 pages. (Jul. 18, 2014).
Madrid, et al., Synthesis and antitubercular activity of phenothiazines with reduced binding to dopamine and serotonin receptors, Bioorganic & Medicinal Chemistry Letters, 17:11: 3014-3017 (2007).
Written Opinion for PCT/EP2014/063446, 6 pages (Jul. 18, 2014).

* cited by examiner

*Primary Examiner* — Samira Jean-Louis
(74) *Attorney, Agent, or Firm* — Brenda Herschbach Jarrell; Robert N. Sahr; Choate Hall & Stewart LLP

(57) ABSTRACT

The present invention relates to the (S)-enantiomer of mepazine, its applicability in therapy, a pharmacological composition comprising (S)-mepazine, and processes for the preparation of (S)-mepazine and one of its intermediates.

19 Claims, 7 Drawing Sheets a b c

(S)-ENANTIOMER OF MEPAZINE

TECHNICAL FIELD OF THE INVENTION

The present invention relates to the (S)-enantiomer of mepazine, its applicability in therapy, a pharmacological composition comprising (S)-mepazine, and processes for the preparation of (S)-mepazine and one of its intermediates.

BACKGROUND OF THE INVENTION

Mepazine, i.e., the compound 10-[(1-methylpiperidin-3-yl)methyl]-10H-phenothiazine, was initially used as a tranquilizer (Lord and Archibald, Can. J. Comp. Med. Vet. Sci., 1957, 21, 391-394). The structurally very similar compounds 10-[2-(1-methylpiperidin-2-yl)ethyl]-2-(methylthio) phenothiazine (thioridazine) and N,N-dimethyl-1-(10H-phenothiazin-10-yl)propan-2-amine (promethazine) are known in the art as antipsychotic drugs and exert sedative effects by acting as dopamine receptor antagonists (Seeman and Lee, Science, 1975, 188, 1217-1219). Recently, it has been found that certain phenothiazine derivatives are inhibitors of a paracaspase, in particular inhibitors of MALT1, and, thus, are useful in treating disorders and diseases in the development of which dysregulation of the activity of the paracaspase (in particular MALT1) plays a crucial role. Exemplary disorders/diseases which are treatable by the phenothiazine derivatives include diffuse-large B cell lymphoma (DLBCL) and multiple sclerosis.

In view of the above, it would be desirable to provide compounds exhibiting an improved therapeutic profile (e.g., improved pharmacological and/or metabolic properties, such as higher activity against a paracaspase and reduced sedative and/or antipsychotic effect). A further object of the present application is the provision of a process for the preparation of such compounds.

SUMMARY OF THE INVENTION

In a first aspect, the present invention provides a compound selected from the group consisting of 10-{[(3S)-1-methylpiperidin-3-yl]methyl}-10H-phenothiazine (the (S)-enantiomer of mepazine, in the following (S)-mepazine) and solvates, salts, isotopically labeled forms, and combinations thereof. In a preferred embodiment, the compound of the invention is the hydrochloride, acetate, or tartrate salt of (S)-mepazine.

In a second aspect, the present invention provides a pharmaceutical composition comprising a compound of the first aspect and a pharmaceutically acceptable excipient.

In a third aspect, the present invention provides a compound of the first aspect or a pharmaceutical composition of the second aspect for inhibiting a paracaspase. In a preferred embodiment, the paracaspase is MALT1.

In a fourth aspect, the present invention provides a compound of the first aspect or a pharmaceutical composition of the second aspect for use in therapy.

In a fifth aspect, the present invention provides a compound of the first aspect or a pharmaceutical composition of the second aspect for use in a method for treating or preventing a disease or disorder which is treatable by an inhibitor of a paracaspase. Preferably, the paracaspase is MALT1. In a preferred embodiment, the disease or disorder to be treated or prevented is cancer, such as a lymphoma, preferably mucosa-associated lymphoid tissue (MALT) lymphoma or diffuse large B-cell lymphoma (DLBCL), such as activated B-cell subtype of diffuse-large B cell lymphoma (ABC-DLBCL). In a further embodiment, the disease or disorder to be treated or prevented is a paracaspase-dependent immune disease, such as an allergic inflammation or an autoimmune disease, e.g., multiple sclerosis.

In a sixth aspect, the present invention provides a process for the preparation of a compound of the first aspect, comprising the step of reacting phenothiazine with a piperidine derivative of the following formula (3)

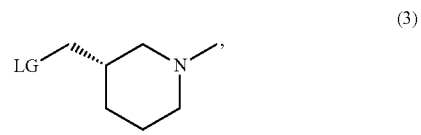

(3)

wherein LG is a leaving group. In a preferred embodiment, the process further comprises the step of converting a tertiary amine of the following formula (2)

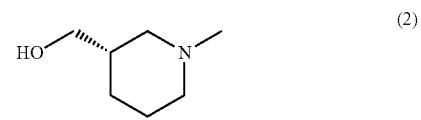

(2)

into the piperidine derivative of formula (3). The tertiary amine of formula (2) may be prepared by converting a carbamate of the following formula (1)

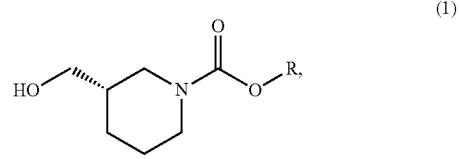

(1)

wherein R is an optionally substituted alkyl, cycloalkyl, heterocyclyl, aryl, or heteroaryl group, into the tertiary amine of formula (2), optionally in the presence of a reducing agent, such as LiAlH$_4$. In one embodiment, the step of reacting phenothiazine with the piperidine derivative of formula (3) and/or the step of converting the tertiary amine of formula (2) into the piperidine derivative of formula (3) is conducted in the presence of a chemical base. In one embodiment, the leaving group (LG) is selected from the group consisting of Br, Cl, mesylate, triflate, and tosylate.

In a seventh aspect, the present invention provides a process for the preparation of a tertiary amine of the following formula (2)

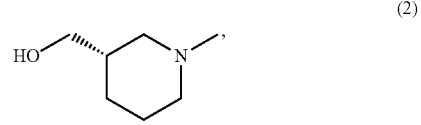

(2)

the method comprising the step of reducing a carbamate of the following formula (1)

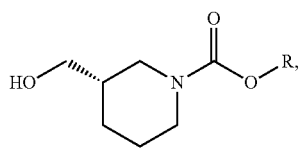

(1)

wherein R is an optionally substituted alkyl, cycloalkyl, heterocyclyl, aryl, or heteroaryl group, with a reducing agent, such as LiAlH$_4$.

DETAILED DESCRIPTION OF THE PRESENT INVENTION

Figure 1:
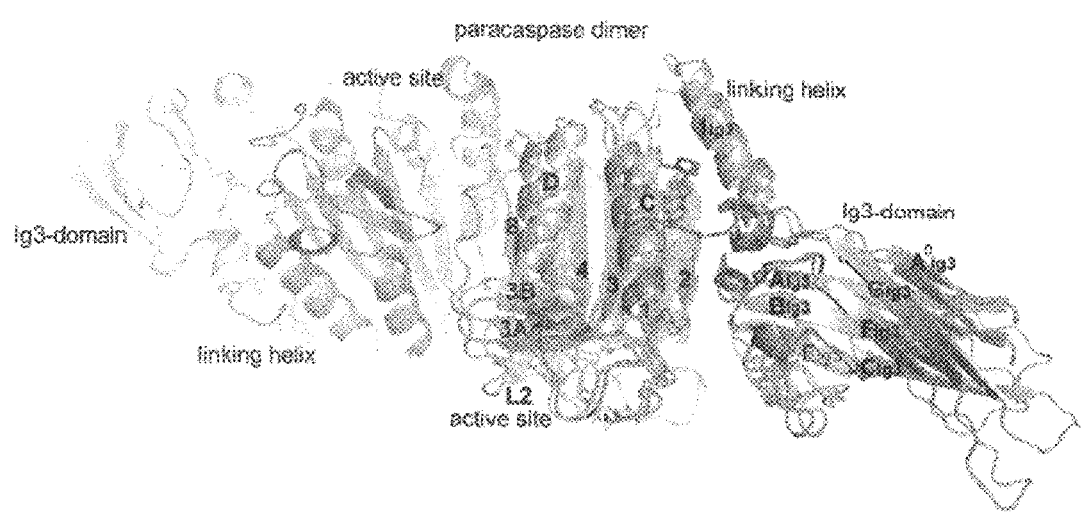
FIG. 1: Thioridazine binds at a position in the interface between the caspase and Ig3 domain connecting helix α1Ig3 of MALT1. (a) Superposition of MALT1$_{Casp-Ig3}$ structure bound to hex-LRSR-peptide (gray) and in complex with thioridazine (dark gray). To show the biological assembly as dimer, the symmetry mate of the thioridazine bound structure is displayed in light gray on the left. (b) The conformational rearrangement of helix αC and αD and subsequently β sheets 3A and 3B is inhibited due to the steric hindrance by thioridazine. (c) Close up view of W580 flipping and the interaction of thioridazine to residue E397. The thioridazine bound and ligand free MALT1 structures are shown in dark gray and light gray, respectively.
Figure 1:
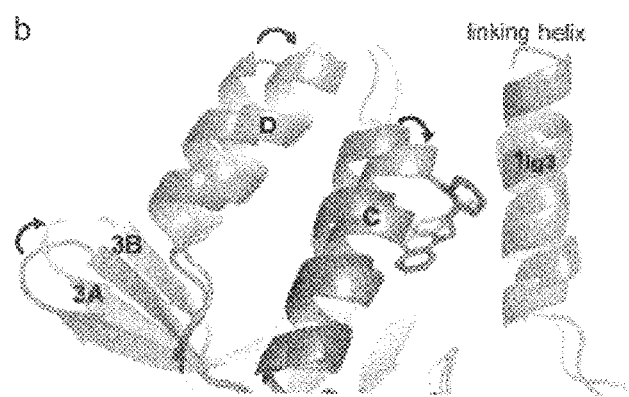
Figure 1:
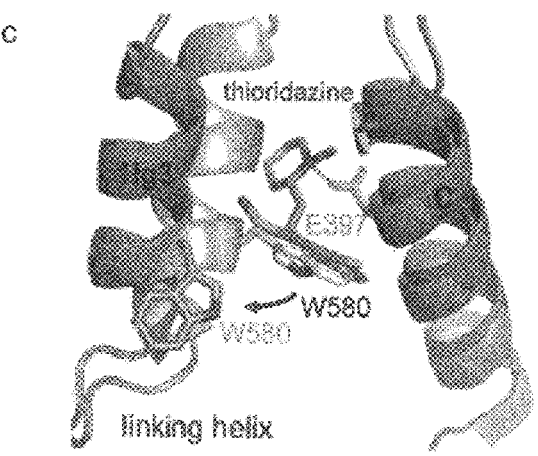

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise. For example, if in one embodiment the compound of the present invention is a tartrate and in another embodiment the compound of the present invention is isotopically labeled, then in yet another embodiment the compound of the present invention may be an isotopically labeled form of (S)-mepazine tartrate. Likewise, if in one embodiment of the process for the preparation of a compound of the present invention the leaving group LG is tosylate and in another embodiment of the process for the preparation of a compound of the present invention the step of reacting phenothiazine with a piperidine derivative of formula (3) is conducted in the presence of a chemical base, then in yet another embodiment of the process for the preparation of a compound of the present invention phenothiazine may be reacted with a piperidine derivative of formula (3), wherein the leaving group LG is tosylate, in the presence of a chemical base.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland (1995).

The practice of the present invention will employ, unless otherwise indicated, conventional methods of chemistry, biochemistry, and recombinant DNA techniques which are explained in the literature in the field (cf., e.g., Molecular Cloning: A Laboratory Manual, $2^{nd}$ Edition, J. Sambrook et al. eds., Cold Spring Harbor Laboratory Press, Cold Spring Harbor 1989; M. B. Smith and J. March, "March's advanced organic chemistry: reactions, mechanisms, and structure", $5^{th}$ edition, John Wiley & Sons, Inc., 2001; "Organikum", $18^{th}$ edition, Deutscher Verlag der Wissenschaften, 1990).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by the context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The term "alkyl" refers to a monoradical of a saturated straight or branched hydrocarbon. Preferably, the alkyl group comprises from 1 to 10 carbon atoms, i.e., 1, 2, 3, 4, 5, 6, 7, 8, 9, or 10 carbon atoms, more preferably 1 to 8 carbon atoms, such as 1 to 6 or 1 to 4 carbon atoms. Exemplary alkyl groups include methyl, ethyl, propyl, isopropyl, butyl, iso-butyl, tert-butyl, n-pentyl, iso-pentyl, sec-pentyl, neo-pentyl, 1,2-dimethyl-propyl, iso-amyl, n-hexyl, iso-hexyl, sec-hexyl, n-heptyl, iso-heptyl, n-octyl, 2-ethylhexyl, n-nonyl, n-decyl, and the like.

The term "alkenyl" refers to a monoradical of an unsaturated straight or branched hydrocarbon having at least one carbon-carbon double bond. Generally, the maximal number of carbon-carbon double bonds in the alkenyl group can be equal to the integer which is calculated by dividing the number of carbon atoms in the alkenyl group by 2 and, if the number of carbon atoms in the alkenyl group is uneven, rounding the result of the division down to the next integer. For example, for an alkenyl group having 9 carbon atoms, the maximum number of carbon-carbon double bonds is 4. Preferably, the alkenyl group has 1 to 4, i.e., 1, 2, 3, or 4, carbon-carbon double bonds. Preferably, the alkenyl group comprises from 2 to 10 carbon atoms, i.e., 1, 2, 3, 4, 5, 6, 7, 8, 9, or 10 carbon atoms, more preferably 2 to 8 carbon atoms, such as 2 to 6 carbon atoms or 2 to 4 carbon atoms. Thus, in a preferred embodiment, the alkenyl group comprises from 2 to 10 carbon atoms and 1, 2, 3, 4, or 5 carbon-carbon double bonds, more preferably it comprises 2 to 8 carbon atoms and 1, 2, 3, or 4 carbon-carbon double bonds, such as 2 to 6 carbon atoms and 1, 2, or 3 carbon-carbon double bonds or 2 to 4 carbon atoms and 1 or 2 carbon-carbon double bonds. The carbon-carbon double bond(s) may be in cis (Z) or trans (E) configuration. Exemplary alkenyl groups include vinyl, 1-propenyl, 2-propenyl (i.e., allyl), 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, and the like. If an alkenyl group is attached to a nitrogen atom, the double bond cannot be alpha to the nitrogen atom.

The term "alkynyl" refers to a monoradical of an unsaturated straight or branched hydrocarbon having at least one carbon-carbon triple bond. Generally, the maximal number of carbon-carbon triple bonds in the alkynyl group can be equal to the integer which is calculated by dividing the number of carbon atoms in the alkynyl group by 2 and, if the number of carbon atoms in the alkynyl group is uneven, rounding the result of the division down to the next integer. For example, for an alkynyl group having 9 carbon atoms, the maximum number of carbon-carbon triple bonds is 4. Preferably, the alkynyl group has 1 to 4, i.e., 1, 2, 3, or 4, more preferably 1 or 2 carbon-carbon triple bonds. Preferably, the alkynyl group comprises from 2 to 10 carbon atoms, i.e., 1, 2, 3, 4, 5, 6, 7, 8, 9, or 10 carbon atoms, more preferably 2 to 8 carbon atoms, such as 2 to 6 carbon atoms or 2 to 4 carbon atoms. Thus, in a preferred embodiment, the alkynyl group comprises from 2 to 10 carbon atoms and 1, 2, 3, 4, or 5 (preferably 1, 2, or 3) carbon-carbon triple bonds, more preferably it comprises 2 to 8 carbon atoms and 1, 2, 3, or 4 (preferably 1 or 2) carbon-carbon triple bonds, such as 2 to 6 carbon atoms and 1, 2 or 3 carbon-carbon triple bonds or 2 to 4 carbon atoms and 1 or 2 carbon-carbon triple bonds. Exemplary alkynyl groups include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 2-heptynyl, 3-heptynyl, 4-heptynyl, 5-heptynyl, 6-heptynyl, 1-octynyl, 2-octynyl, 3-octynyl, 4-octynyl, 5-octynyl, 6-octynyl, 7-octynyl, 1-nonylyl, 2-nonynyl, 3-nonynyl, 4-nonynyl, 5-nonynyl, 6-nonynyl, 7-nonynyl, 8-nonynyl, 1-decynyl, 2-decynyl, 3-decynyl, 4-decynyl, 5-decynyl, 6-decynyl, 7-decynyl, 8-decynyl, 9-decynyl, and the like. If an alkynyl group is attached to a nitrogen atom, the triple bond cannot be alpha to the nitrogen atom.

The term "cycloalkyl" represents cyclic non-aromatic versions of "alkyl" with preferably 3 to 14 carbon atoms, such as 3 to 10 carbon atoms, i.e., 3, 4, 5, 6, 7, 8, 9, or 10 carbon atoms, more preferably 3 to 6 carbon atoms. The cycloalkyl group may be unsaturated (i.e., it may contain one or more carbon-carbon double bonds). In one embodiment, the cycloalkyl group is saturated (i.e., it does not contain carbon-carbon double bonds). Exemplary cycloalkyl groups include cyclopropyl, cyclopropenyl, cyclobutyl, cyclobutenyl, cyclopentyl, cyclopentenyl, cyclohexyl, cyclohexenyl, cycloheptyl, cycloheptenyl, cyclooctyl, cyclobutenyl, cyclononyl, cyclononenyl, cylcodecyl, cylcodecenyl, and adamantyl. The term "cycloalkyl" is also meant to include bicyclic and tricyclic versions thereof. If bicyclic rings are formed it is preferred that the respective rings are connected to each other at two adjacent carbon atoms, however, alternatively the two rings are connected via the same carbon atom, i.e., they form a spiro ring system or they form "bridged" ring systems. Preferred examples of cycloalkyl include $C_3$-$C_8$-cycloalkyl, in particular cyclopropyl, cyclobutyl, cyclopentyl, cyclohexyl, cycloheptyl, cyclooctyl, spiro[3,3]heptyl, spiro[3,4]octyl, spiro[4,3]octyl, bicyclo[4.1.0]heptyl, bicyclo[3.2.0]heptyl, bicyclo[2.2.1]heptyl, bicyclo[2.2.2]octyl, bicyclo[5.1.0]octyl, and bicyclo[4.2.0]octyl.

The term "aryl" or "aromatic ring" refers to a monoradical of an aromatic cyclic hydrocarbon. Preferably, the aryl group contains 3 to 14 carbon atoms which can be arranged in one ring (e.g., phenyl) or two or more condensed rings (e.g., naphthyl). Exemplary aryl groups include cyclopropenylium, cyclopentadienyl, phenyl, indenyl, naphthyl, azulenyl, fluorenyl, anthryl, and phenanthryl. Preferably, "aryl" refers to a monocyclic ring containing 6 carbon atoms or an aromatic bicyclic ring system containing 10 carbon atoms. Preferred examples are phenyl and naphthyl.

The term "heteroaryl" or "heteroaromatic ring" means an aryl group as defined above in which one or more carbon atoms in the aryl group are replaced by heteroatoms of O, S, or N. Preferably, heteroaryl refers to a five or six-membered aromatic monocyclic ring wherein 1, 2, or 3 carbon atoms are replaced by the same or different heteroatoms of O, N, or S. Alternatively, it means an aromatic bicyclic or tricyclic ring system wherein 1, 2, 3, 4, or 5 carbon atoms are replaced with the same or different heteroatoms of O, N, or S. Preferably, in each ring of the heteroaryl group the maximum number of O atoms is 1, the maximum number of S atoms is 1, and the maximum total number of O and S atoms is 2. Exemplary heteroaryl groups include furanyl, thienyl, oxazolyl, isoxazolyl, oxadiazolyl (1,2,5- and 1,2,3-), pyrrolyl, imidazolyl, pyrazolyl, triazolyl (1,2,3- and 1,2,4-), tetrazolyl, thiazolyl, isothiazolyl, thiadiazolyl (1,2,3- and 1,2,5-), pyridyl, pyrimidinyl, pyrazinyl, triazinyl (1,2,3-, 1,2,4-, and 1,3,5-), benzofuranyl (1- and 2-), indolyl, isoindolyl, benzothienyl (1- and 2-), 1H-indazolyl, benzimidazolyl, benzoxazolyl, indoxazinyl, benzisoxazolyl, benzothiazolyl, benzisothiazolyl, benzotriazolyl, quinazolinyl, isoquinolinyl, benzodiazinyl, quinoxalinyl, quinazolinyl, benzotriazinyl (1,2,3- and 1,2,4-benzotriazinyl), pyridazinyl, phenoxazinyl, thiazolopyridinyl, pyrrolothiazolyl, phenothiazinyl, isobenzofuranyl, chromenyl, xanthenyl, phenoxathiinyl, pyrrolizinyl, indolizinyl, indazolyl, purinyl, quinolizinyl, phthalazinyl, naphthyridinyl (1,5-, 1,6-, 1,7-, 1,8-, and 2,6-), cinnolinyl, pteridinyl, carbazolyl, phenanthridinyl, acridinyl, perimidinyl, phenanthrolinyl (1,7-, 1,8-, 1,10-, 3,8-, and 4,7-), phenazinyl, oxazolopyridinyl, isoxazolopyridinyl, pyrrolooxazolyl, and pyrrolopyrrolyl. Exemplary 5- or 6-membered heteroaryl groups include furanyl, thienyl, oxazolyl, isoxazolyl, oxadiazolyl (1,2,5- and 1,2,3-), pyrrolyl, imidazolyl, pyrazolyl, triazolyl (1,2,3- and 1,2,4-), thiazolyl, isothiazolyl, thiadiazolyl (1,2,3- and 1,2,5-), pyridyl, pyrimidinyl, pyrazinyl, triazinyl (1,2,3-, 1,2,4-, and 1,3,5-), and pyridazinyl.

The term "heterocyclyl" or "heterocyclic ring" means a cycloalkyl group as defined above in which from 1, 2, 3, or 4 carbon atoms in the cycloalkyl group are replaced by heteroatoms of O, S, or N. Preferably, in each ring of the heterocyclyl group the maximum number of O atoms is 1, the maximum number of S atoms is 1, and the maximum total number of O and S atoms is 2. The term "heterocyclyl" is also meant to encompass partially or completely hydrogenated forms (such as dihydro, tetrahydro or perhydro forms) of the above-mentioned heteroaryl groups. Exemplary heterocyclyl groups include morpholino, isochromanyl, chromanyl, pyrrolidinyl, imidazolidinyl, pyrazolidinyl, piperidinyl, piperazinyl, indolinyl, isoindolinyl, di- and tetrahydrofuranyl, di- and tetrahydrothienyl, di- and tetrahydrooxazolyl, di- and tetrahydroisoxazolyl, di- and tetrahydrooxadiazolyl (1,2,5- and 1,2,3-), dihydropyrrolyl, dihydroimidazolyl, dihydropyrazolyl, di- and tetrahydrotriazolyl (1,2,3- and 1,2,4-), di- and tetrahydrothiazolyl, di- and tetrahydrothiazolyl, di- and tetrahydrothiadiazolyl (1,2,3- and 1,2,5-), di- and tetrahydropyridyl, di- and tetrahydropyrimidinyl, di- and tetrahydropyrazinyl, di- and tetrahydrotriazinyl (1,2,3-, 1,2,4-, and 1,3,5-), di- and tetrahydrobenzofuranyl (1- and 2-), di- and tetrahydroindolyl, di- and tetrahydroisoindolyl, di- and tetrahydrobenzothienyl (1- and 2), di- and tetrahydro-1H-indazolyl, di- and tetrahydrobenzimidazolyl, di- and tetrahydrobenzoxazolyl, di- and tetrahydroindoxazinyl, di- and tetrahydrobenzisoxazolyl, di- and tetrahydrobenzothiazolyl, di- and tetrahydrobenzisothiazolyl, di- and tetrahydrobenzotriazolyl, di- and tetrahydroquinolinyl, di- and tetrahydroisoquinolinyl, di- and tetrahydrobenzodiazinyl, di- and tetrahydroquinoxalinyl, di- and tetrahydroquinazolinyl, di- and tetrahydrobenzotriazinyl (1,2,3- and 1,2,4-), di- and tetrahydropyridazinyl, di- and tetrahydrophenoxazinyl, di- and tetrahydrothiazolopyridinyl (such as 4,5,6-7-tetrahydro[1,3]thiazolo[5,4-c]pyridinyl or 4,5,6-7-tetrahydro[1,3]thiazolo[4,5-c]pyridinyl, e.g., 4,5,6-7-tetrahydro[1,3]thiazolo[5,4-c]pyridin-2-yl or 4,5,6-7-tetrahydro[1,3]thiazolo[4,5-e]pyridin-2-yl), di- and tetrahydropyrrolothiazolyl (such as 5,6-dihydro-4H-pyrrolo[3,4-d][1,3]thiazolyl), di- and tetrahydrophenothiazinyl, di- and tetrahydroisobenzofuranyl, di- and tetrahydrochromenyl, di- and tetrahydroxanthenyl, di- and tetrahydrophenoxathiinyl, di- and tetrahydropyrrolizinyl, di- and tetrahydroindolizinyl, di- and tetrahydroindazolyl, di- and tetrahydropurinyl, di- and tetrahydroquinolizinyl, di- and tetrahydrophthalazinyl, di- and tetrahydronaphthyridinyl (1,5-, 1,6-, 1,7-, 1,8-, and 2,6-), di- and tetrahydrocinnolinyl, di- and tetrahydropteridinyl, di- and tetrahydrocarbazolyl, di- and tetrahydrophenanthridinyl, di- and tetrahydroacridinyl, di- and tetrahydroperimidinyl, di- and tetrahydrophenanthrolinyl (1,7-, 1,8-, 1,10-, 3,8-, and 4,7-), di- and tetrahydrophenazinyl, di- and tetrahydrooxazolopyridinyl, di- and tetrahydroisoxazolopyridinyl, di- and tetrahydropyrrolooxazolyl, and di- and tetrahydropyrrolopyrrolyl. Exemplary 5- or 6-membered heterocyclyl groups include morpholino, pyrrolidinyl, imidazolidinyl, pyrazolidinyl, piperidinyl, piperazinyl, di- and tetrahydrofuranyl, di- and tetrahydrothienyl, di- and tetrahydrooxazolyl, di- and tetrahydroisoxazolyl, di- and tetrahydrooxadiazolyl (1,2,5- and 1,2,3-), dihydropyrrolyl, dihydroimidazolyl, dihydropyrazolyl, di- and tetrahydrotriazolyl (1,2,3- and 1,2,4-), di- and tetrahydrothiazolyl, di- and tetrahydroisothiazolyl, di- and tetrahydrothiadiazolyl (1,2,3- and 1,2,5-), di- and tetrahydropyridyl, di- and tetrahydropyrimidinyl, di- and tetrahydropyrazinyl, di- and tetrahydrotriazinyl (1,2,3-, 1,2,4-, and 1,3,5-), and di- and tetrahydropyridazinyl.

The term "halogen" or "halo" means fluoro, chloro, bromo, or iodo.

The term "azido" means —$N_3$.

The term "optionally substituted" indicates that one or more hydrogen atom(s) is/are replaced with a group (i.e., a $1^{st}$ level substituent) different from hydrogen such as alkyl (preferably, $C_{1-6}$ alkyl), alkenyl (preferably, $C_{2-6}$ alkenyl), alkynyl (preferably, $C_{2-6}$ alkynyl), aryl (preferably, 3- to 14-membered aryl), heteroaryl (preferably, 3- to 14-membered heteroaryl), cycloalkyl (preferably, 3- to 14-membered cycloalkyl), heterocyclyl (preferably, 3- to 14-membered heterocyclyl), halogen, —CN, azido, —NO$_2$, —OR$^{71}$, —N(R$^{72}$)(R$^{73}$), —ON(R$^{72}$)(R$^{73}$), —N$^+$(—O$^-$)(R$^{72}$)(R$^{73}$), —S(O)$_{0-2}$R$^{71}$, —S(O)$_{0-2}$OR$^{71}$, —OS(O)$_{0-2}$R$^{71}$, —OS(O)$_{0-2}$OR$^{71}$, —S(O)$_{0-2}$N(R$^{72}$)(R$^{73}$), —OS(O)$_{0-2}$N(R$^{72}$)(R$^{73}$), —N(R$^{71}$)S(O)$_{0-2}$R$^{71}$, —NR$^{71}$S(O)$_{0-2}$OR$^{71}$, —NR$^{71}$S(O)$_{0-2}$N(R$^{72}$)(R$^{73}$), —C(=X$^1$)R$^{71}$, —C(=X$^1$)X$^1$R$^{71}$, —X$^1$C(=X$^1$)R$^{71}$, and —X$^1$C(=X$^1$)X$^1$R$^{71}$, wherein each of the alkyl, alkenyl, alkynyl, aryl, heteroaryl, cycloalkyl, and heterocyclyl groups of the 1$^{st}$ level substituent may themselves be substituted by one, two or three substituents (i.e., a 2$^{nd}$ level substituent) selected from the group consisting of C$_{1-6}$ alkyl, C$_{2-6}$ alkenyl, C$_{2-6}$ yl, 3- to 14-membered aryl, 3- to 14-membered heteroaryl, 3- to 14-membered cycloalkyl, 3- to 14-membered heterocyclyl, halogen, —CF$_3$, —CN, azido, —NO$_2$, —OR$^{81}$, —N(R$^{82}$)(R$^{83}$), —ON(R$^{82}$)(R$^{83}$), —N$^+$(—O$^-$)(R$^{82}$)(R$^{83}$), —S(O)$_{0-2}$R$^{81}$, —S(O)$_{0-2}$OR$^{81}$, —OS(O)$_{0-2}$R$^{81}$, —OS(O)$_{0-2}$OR$^{81}$, —S(O)$_{0-2}$N(R$^{82}$)(R$^{83}$), —OS(O)$_{0-2}$N(R$^{82}$)(R$^{83}$), —N(R$^{81}$)S(O)$_{0-2}$R$^{81}$, —NR$^{82}$S(O)$_{0-2}$OR$^{81}$, —NR$^{81}$S(O)$_{0-2}$N(R$^{82}$)(R$^{83}$), —C(=X$^2$)R$^{81}$, —C(=X$^2$)X$^2$R$^{81}$, —X$^2$C(=X$^2$)R$^{81}$, and —X$^2$C(=X$^2$)X$^2$R$^{81}$, wherein each of the C$_{1-6}$ alkyl, C$_{2-6}$ alkenyl, C$_{2-6}$ alkynyl, 3- to 14-membered aryl, 3- to 14-membered heteroaryl, 3- to 14-membered cycloalkyl, 3- to 14-membered heterocyclyl groups of the 2$^{nd}$ level substituent is optionally substituted with one, two or three substituents (i.e., a 3$^{rd}$ level substituent) independently selected from the group consisting of C$_{1-3}$ alkyl, halogen, —CF$_3$, —CN, azido, —NO$_2$, —OH, —O(C$_{1-3}$ alkyl), —S(C$_{1-3}$ alkyl), —NH$_2$, —NH(C$_{1-3}$ alkyl), —N(C$_{1-3}$ alkyl)$_2$, —NHS(O)$_2$(C$_{1-3}$ alkyl), —S(O)$_2$NH$_{2-z}$(C$_{1-3}$ alkyl)$_z$, —C(=O)OH, —C(=O)O(C$_{1-3}$ alkyl), —C(=O)NH$_{2-z}$(C$_{1-3}$ alkyl)$_z$, —NHC(=O)(C$_{1-3}$ alkyl), —NHC(=NH)NH$_{2-z}$(C$_{1-3}$ alkyl)$_z$, and —N(C$_{1-3}$ alkyl)C(=NH)NH$_{2-z}$(C$_{1-3}$ alkyl)$_z$, wherein z is 0, 1, or 2 and C$_{1-3}$ alkyl is methyl, ethyl, propyl or isopropyl;
wherein R$^{71}$, R$^{72}$, and R$^{73}$ are independently selected from the group consisting of —H, C$_{1-6}$ alkyl, C$_{2-6}$ alkenyl, C$_{2-6}$ alkynyl, 3- to 7-membered cycloalkyl, 5- or 6-membered aryl, 5- or 6-membered heteroaryl, and 3- to 7-membered heterocyclyl, wherein each of the alkyl, alkenyl, alkynyl, cycloalkyl, aryl, heteroaryl, and heterocyclyl groups is optionally substituted with one, two or three substituents selected from the group consisting of C$_{1-3}$ alkyl, halogen, —CF$_3$, —CN, azido, —NO$_2$, —OH, —OH, —O(C$_{1-3}$ alkyl), —S(C$_{1-3}$ alkyl), —NH$_2$, —NH(C$_{1-3}$ alkyl), —N(C$_{1-3}$ alkyl)$_2$, —NHS(O)$_2$(C$_{1-3}$ alkyl), —S(O)$_2$NH$_{2-z}$(C$_{1-3}$ alkyl)$_z$, —C(=O)OH, —C(=O)O(C$_{1-3}$ alkyl), —C(=O)NH$_{2-z}$(C$_{1-3}$ alkyl)$_z$, —NHC(=O)(C$_{1-3}$ alkyl), —NHC(=NH)NH$_{2-z}$(C$_{1-3}$ alkyl)$_z$, and —N(C$_{1-3}$ alkyl)C(=NH)NH$_{2-z}$(C$_{1-3}$ alkyl)$_z$, wherein z is 0, 1, or 2 and C$_{1-3}$ alkyl is methyl, ethyl, propyl or isopropyl, or R$^{72}$ and R$^{73}$ may join together with the nitrogen atom to which they are attached to form a 5- or 6-membered ring, which is optionally substituted with one, two or three substituents selected from the group consisting of C$_{1-3}$ alkyl, halogen, —CF$_3$, —CN, azido, —NO$_2$, —OH, —OH, —O(C$_{1-3}$ alkyl), —S(C$_{1-3}$ alkyl), —NH$_2$, —NH(C$_{1-3}$ alkyl), —N(C$_{1-3}$ alkyl)$_2$, —NHS(O)$_2$(C$_{1-3}$ alkyl), —S(O)$_2$NH$_{2-z}$(C$_{1-3}$ alkyl)$_z$, —C(=O)OH, —C(=O)O(C$_{1-3}$ alkyl), —C(=O)NH$_{2-z}$(C$_{1-3}$ alkyl)$_z$, —NHC(=O)(C$_{1-3}$ alkyl), —NHC(=NH)NH$_{2-z}$(C$_{1-3}$ alkyl)$_z$, and —N(C$_{1-3}$ alkyl)C(=NH)NH$_{2-z}$(C$_{1-3}$ alkyl)$_z$, wherein z is 0, 1, or 2 and C$_{1-3}$ alkyl is methyl, ethyl, propyl or isopropyl;

R$^{81}$, R$^{82}$, and R$^{83}$ are independently selected from the group consisting of —H, C$_{1-4}$ alkyl, C$_{2-4}$ alkenyl, C$_{2-4}$ alkynyl, 3- to 6-membered cycloalkyl, 5- or 6-membered aryl, 5- or 6-membered heteroaryl, and 3- to 6-membered heterocyclyl, wherein each of the alkyl, alkenyl, alkynyl, cycloalkyl, aryl, heteroaryl, and heterocyclyl groups is optionally substituted with one, two or three substituents selected from the group consisting of C$_{1-3}$ alkyl, halogen, —CF$_3$, —CN, azido, —NO$_2$, —OH, —O(C$_{1-3}$ alkyl), —S(C$_{1-3}$ alkyl), —NH$_2$, —NH(C$_{1-3}$ alkyl), —N(C$_{1-3}$ alkyl)$_2$, —NHS(O)$_2$(C$_{1-3}$ alkyl), —S(O)$_2$NH$_{2-z}$(C$_{1-3}$ alkyl)$_z$, —C(=O)OH, —C(=O)O(C$_{1-3}$ alkyl), —C(=O)NH$_{2-z}$(C$_{1-3}$ alkyl)$_z$, —NHC(=O)(C$_{1-3}$ alkyl), —NHC(=NH)NH$_{2-z}$(C$_{1-3}$ alkyl)$_z$, and —N(C$_{1-3}$ alkyl)C(=NH)NH$_{2-z}$(C$_{1-3}$ alkyl)$_z$, wherein z is 0, 1, or 2 and C$_{1-3}$ alkyl is methyl, ethyl, propyl or isopropyl, or R$^{82}$ and R$^{83}$ may join together with the nitrogen atom to which they are attached to form a 5- or 6-membered ring, which is optionally substituted with one, two or three substituents selected from the group consisting of C$_{1-3}$ alkyl, halogen, —CF$_3$, —CN, azido, —NO$_2$, —OH, —O(C$_{1-3}$ alkyl), —S(C$_{1-3}$ alkyl), —NH$_2$, —NH(C$_{1-3}$ alkyl), —N(C$_{1-3}$ alkyl)$_2$, —NHS(O)$_2$(C$_{1-3}$ alkyl), —S(O)$_2$NH$_{2-z}$(C$_{1-3}$ alkyl)$_z$, —C(=O)OH, —C(=O)O(C$_{1-3}$ alkyl), —C(=O)NH$_{2-z}$(C$_{1-3}$ alkyl)$_z$, —NHC(=O)(C$_{1-3}$ alkyl), —NHC(=NH)NH$_{2-z}$(C$_{1-3}$ alkyl)$_z$, and —N(C$_{1-3}$ alkyl)C(=NH)NH$_{2-z}$(C$_{1-3}$ alkyl)$_z$, wherein z is 0, 1, or 2 and C$_{1-3}$ alkyl is methyl, ethyl, propyl or isopropyl;

X$^1$ and X$^2$ are independently selected from O, S, and NR$^{84}$, wherein R$^{84}$ is —H or C$_{1-3}$ alkyl.

Typical 1$^{st}$ level substituents are preferably selected from the group consisting of C$_{1-6}$ alkyl, C$_{2-6}$ alkenyl, C$_{2-6}$ alkynyl, 3- to 14-membered (such as 5- or 6-membered) aryl, 3- to 14-membered (such as 5- or 6-membered) heteroaryl, 3- to 14-membered (such as 3- to 7-membered) cycloalkyl, 3- to 14-membered (such as 3- to 7-membered) heterocyclyl, halogen, —CN, azido, —NO$_2$, —OR$^{71}$, —N(R$^{72}$)(R$^{73}$), —S(O)$_{0-2}$R$^{71}$, —S(O)$_{0-2}$OR$^{71}$, —OS(O)$_{0-2}$R$^{71}$, —OS(O)$_{0-2}$OR$^{71}$, —S(O)$_{0-2}$N(R$^{72}$)(R$^{73}$), —OS(O)$_{0-2}$N(R$^{72}$)(R$^{73}$), —N(R$^{71}$)S(O)$_{0-2}$R$^{71}$, —NR$^{71}$S(O)$_{0-2}$OR$^{71}$, —C(=X$^1$)R$^{71}$, —C(=X$^1$)X$^1$R$^{71}$, —X$^1$C(=X$^1$)R$^{71}$, and —X$^1$C(=X$^1$)X$^1$R$^{71}$, such as C$_{1-4}$ alkyl, C$_{2-4}$ alkenyl, C$_{2-4}$ alkynyl, 5- or 6-membered aryl, 5- or 6-membered heteroaryl, 3- to 7-membered cycloalkyl, 3- to 7-membered heterocyclyl, halogen, —CF$_3$, —CN, azido, —NO$_2$, —OH, —O(C$_{1-3}$ alkyl), —S(C$_{1-3}$ alkyl), —NH$_2$, —NH(C$_{1-3}$ alkyl), —N(C$_{1-3}$ alkyl)$_2$, —NHS(O)$_2$(C$_{1-3}$ alkyl), —S(O)$_2$NH$_{2-z}$(C$_{1-3}$ alkyl)$_z$, —C(=O)OH, —C(=O)O(C$_{1-3}$ alkyl), —C(=O)NH$_{2-z}$(C$_{1-3}$ alkyl)$_z$, —NHC(=O)(C$_{1-3}$ alkyl), —NHC(=NH)NH$_{2-z}$(C$_{1-3}$ alkyl)$_z$, and —N(C$_{1-3}$ alkyl)C(=NH)NH$_{2-z}$(C$_{1-3}$ alkyl)$_z$, wherein z is 0, 1, or 2 and C$_{1-3}$ alkyl is methyl, ethyl, propyl or isopropyl; X$^1$ is independently selected from O, S, NH and N(CH$_3$); and R$^{71}$, R$^{72}$, and R$^{73}$ are as defined above or, preferably, are independently selected from the group consisting of —H, C$_{1-4}$ alkyl, C$_{2-4}$ alkenyl, C$_{2-4}$ alkynyl, 5- or 6-membered cycloalkyl, 5- or 6-membered aryl, 5- or 6-membered heteroaryl, and 5- or 6-membered heterocyclyl, wherein each of the alkyl, alkenyl, alkynyl, cycloalkyl, aryl, heteroaryl, and heterocyclyl groups is optionally substituted with one, two or three substituents selected from the group consisting of C$_{1-3}$ alkyl, halogen, —CF$_3$, —CN, azido, —NO$_2$, —OH, —O(C$_{1-3}$ alkyl), —S(C$_{1-3}$ alkyl), —NH$_2$, —NH(C$_{1-3}$ alkyl), —N(C$_{1-3}$ alkyl)$_2$, —NHS(O)$_2$(C$_{1-3}$ alkyl), —S(O)$_2$NH$_{2-z}$(C$_{1-3}$ alkyl)$_z$, —C(=O)OH, —C(=O)O(C$_{1-3}$ alkyl), —C(=O)NH$_{2-z}$(C$_{1-3}$ alkyl)$_z$, —NHC(=O)(C$_{1-3}$ alkyl), —NHC(=NH)NH$_{2-z}$(C$_{1-3}$ alkyl)$_z$, and —N(C$_{1-3}$ alkyl)C(=NH)NH$_{2-z}$(C$_{1-3}$ alkyl)$_z$, wherein z is 0, 1, or 2 and C$_{1-3}$ alkyl is methyl, ethyl, propyl or isopropyl; or R$^{72}$ and R$^{73}$ may join together with the nitrogen atom to which they are attached to form a 5- or 6-membered ring, which is optionally substituted with one, two or three substituents selected from the group consisting of $C_{1-3}$ alkyl, halogen, —$CF_3$, —CN, azido, —$NO_2$, —OH, —O($C_{1-3}$ alkyl), —S($C_{1-3}$ alkyl), —$NH_2$, —NH($C_{1-3}$ alkyl), —N($C_{1-3}$ alkyl)$_2$, —NHS(O)$_2$($C_{1-3}$ alkyl), —S(O)$_2$NH$_{2-z}$($C_{1-3}$ alkyl)$_z$, —C(=O)OH, —C(=O)O($C_{1-3}$ alkyl), —C(=O)NH$_{2-z}$($C_{1-3}$ alkyl)$_z$, —NHC(=O)($C_{1-3}$ alkyl), —NHC(=NH)NH$_{2-z}$($C_{1-3}$ alkyl)$_z$, and —N($C_{1-3}$ alkyl)C(=NH)NH$_{2-z}$($C_{1-3}$ alkyl)$_z$, wherein z is 0, 1, or 2 and $C_{1-3}$ alkyl is methyl, ethyl, propyl or isopropyl.

Typical $2^{nd}$ level substituents are preferably selected from the group consisting of $C_{1-4}$ alkyl, $C_{2-4}$ alkenyl, $C_{2-4}$ alkynyl, 5- or 6-membered aryl, 5- or 6-membered heteroaryl, 5- or 6-membered cycloalkyl, 5- or 6-membered heterocyclyl, halogen, —$CF_3$, —CN, azido, —$NO_2$, —OH, —O($C_{1-3}$ alkyl), —S($C_{1-3}$ alkyl), —$NH_2$, —NH($C_{1-3}$ alkyl), —N($C_{1-3}$ alkyl)$_2$, —NHS(O)$_2$($C_{1-3}$ alkyl), —S(O)$_2$NH$_{2-z}$($C_{1-3}$ alkyl)$_z$, —C(=O)OH, —C(=O)O($C_{1-3}$ alkyl), —C(=O)NH$_{2-z}$($C_{1-3}$ alkyl)$_z$, —NHC(=O)($C_{1-3}$ alkyl), —NHC(=NH)NH$_{2-z}$($C_{1-3}$ alkyl)$_z$, and —N($C_{1-3}$ alkyl)C(=NH)NH$_{2-z}$($C_{1-3}$ alkyl)$_z$, wherein z is 0, 1, or 2 and $C_{1-3}$ alkyl is methyl, ethyl, propyl or isopropyl.

Typical $3^{rd}$ level substituents are preferably selected from the group consisting of phenyl, furanyl, pyrrolyl, thienyl, imidazolyl, oxazolyl, isoxazolyl, thiazolyl, pyridyl, pyrazinyl, pyrimidinyl, pyridazinyl, partially and completely hydrogenated forms of the forgoing groups, morpholino, $C_{1-3}$ alkyl, halogen, —$CF_3$, —OH, —$OCH_3$, —$SCH_3$, —NH$_{2-z}$($CH_3$)$_z$, —C(=O)OH, and —C(=O)$OCH_3$, wherein z is 0, 1, or 2.

The term "aromatic" as used in the context of cyclic hydrocarbons (with or without heteroatom(s) in the cyclic structure) means that the whole molecule has to be aromatic. For example, if a monocyclic aryl is hydrogenated (either partially or completely) the resulting hydrogenated cyclic structure is classified as cycloalkyl for the purposes of the present invention. Likewise, if a bi- or polycyclic aryl (such as naphthyl) is hydrogenated the resulting hydrogenated bi- or polycyclic structure (such as 1,2-dihydronaphthyl) is classified as cycloalkyl for the purposes of the present invention (even if one ring, such as in 1,2-dihydronaphthyl, is still aromatic). A similar distinction is made within the present application between heteroaryl and heterocyclyl. For example, indolinyl, i.e., a dihydro variant of indolyl, is classified as heterocyclyl for the purposes of the present invention, since only one ring of the bicyclic structure is aromatic and one of the ring atoms is a heteroatom.

The phrase "partially hydrogenated form" of an unsaturated compound or group as used herein means that part of the unsaturation has been removed by formally adding hydrogen to the initially unsaturated compound or group without removing all unsaturated moieties. The phrase "completely hydrogenated form" of an unsaturated compound or group is used herein interchangeably with the term "perhydro" and means that all unsaturation has been removed by formally adding hydrogen to the initially unsaturated compound or group. For example, partially hydrogenated forms of a 5-membered heteroaryl group (containing 2 double bonds in the ring, such as furan) include dihydro forms of said 5-membered heteroaryl group (such as 2,3-dihydrofuran or 2,5-dihydrofuran), whereas the tetrahydro form of said 5-membered heteroaryl group (e.g., tetrahydrofuran, i.e., THF) is a completely hydrogenated (or perhydro) form of said 5-membered heteroaryl group. Likewise, for a 6-membered heteroaryl group having 3 double bonds in the ring (such as pyridyl), partially hydrogenated forms include di- and tetrahydro forms (such as di- and tetrahydropyridyl), whereas the hexahydro form (such as piperidinyl in case of the heteroaryl pyridyl) is the completely hydrogenated (or perhydro) derivative of said 6-membered heteroaryl group. Consequently, a hexahydro form of an aryl or heteroaryl can only be considered a partially hydrogenated form according to the present invention if the aryl or heteroaryl contains at least 4 unsaturated moieties consisting of double and triple bonds between ring atoms.

The term "optional" or "optionally" as used herein means that the subsequently described event, circumstance or condition may or may not occur, and that the description includes instances where said event, circumstance, or condition occurs and instances in which it does not occur.

"Isomers" are compounds having the same molecular formula but differ in structure ("structural isomers") or in the geometrical positioning of the functional groups and/or atoms ("stereoisomers"). "Enantiomers" are a pair of stereoisomers which are non-superimposable mirror-images of each other. A "racemic mixture" or "racemate" contains a pair of enantiomers in equal amounts and is denoted by the prefix (±). "Diastereomers" are stereoisomers which are non-superimposable mirror-images of each other. "Tautomers" are structural isomers of the same chemical substance that spontaneously interconvert with each other, even when pure.

The term "solvate" as used herein refers to an addition complex of a dissolved material in a solvent (such as an organic solvent (e.g., an aliphatic alcohol (such as methanol, ethanol, n-propanol, isopropanol), acetone, acetonitrile, ether, and the like), water or a mixture of two or more of these liquids), wherein the addition complex exists in the form of a crystal or mixed crystal. The amount of solvent contained in the addition complex may be stoichiometric or non-stoichiometric. A "hydrate" is a solvate wherein the solvent is water.

In isotopically labeled compounds one or more atoms are replaced by a corresponding atom having the same number of protons but differing in the number of neutrons. For example, a hydrogen atom may be replaced by a deuterium atom. Exemplary isotopes which can be used in the compounds and processes of the present invention include deuterium, $^{11}C$, $^{13}C$, $^{14}C$, $^{15}N$, $^{18}F$, $^{32}S$, $^{36}Cl$, and $^{125}I$.

The term "half-life" relates to the period of time which is needed to eliminate half of the activity, amount, or number of molecules. In the context of the present invention, the half-life of a compound of the present invention is indicative for the stability of said compound.

The terms "patient", "individual", or "animal" relate to mammals. For example, mammals in the context of the present invention are humans, non-human primates, domesticated animals such as dogs, cats, sheep, cattle, goats, pigs, horses etc., laboratory animals such as mice, rats, rabbits, guinea pigs, etc. as well as animals in captivity such as animals of zoos. The term "animal" as used herein also includes humans.

The expression "disease or disorder which is treatable by an inhibitor of a paracaspase" as used herein relates to a disease/disorder which is associated with deregulated, in particular constitutive, proteolytic activity of a paracaspase compared to the state in a healthy individual. In one embodiment, the deregulated, in particular constitutive, proteolytic activity of a paracaspase is caused by an activating (e.g., oncogenic) mutation of CARMA1. In one embodiment, the deregulated, in particular constitutive, proteolytic activity of a paracaspase is caused by a constitutive receptor signaling, preferably, by a constitutive B or T cell antigen receptor signaling. In one embodiment, the deregulated, in particular constitutive, proteolytic activity of a paracaspase is caused by an activating mutation in a regulator (e.g., activator) of the paracaspase and/or in a regulator (e.g., activator) of the antigen receptor signaling, e.g., in a regulator (e.g., activator) of the B cell antigen receptor signaling, such as CD79A and/or CD79B. In a preferred embodiment, the paracaspase is MALT1.

The expression "constitutive activity" of a molecule (such as an enzyme or receptor) as used herein means that the molecule exerts its biological activity (such as proteolytic activity) in the absence of a ligand bound to the molecule.

The expression "deregulated activity" of an enzyme or receptor as used herein means that the biological activity of the enzyme or receptor is increased (or even constitutive) since (i) one or more inhibitory regulator molecules of the enzyme or receptor which normally limit the activity of the enzyme or receptor with respect to (1) the effectiveness of the enzyme or receptor (wherein the effectiveness may be expressed as moles of substrate converted per time unit or release of second messenger(s) per time unit) and/or (2) the time period during which the enzyme or receptor is active are altered (e.g., mutated or inhibited), thereby decreasing (or even abolishing) the activity of the inhibitory regulator molecules, and/or (ii) one or more activating regulator molecules of the enzyme or receptor which increase the activity of the enzyme or receptor with respect to (1) the effectiveness of the enzyme or receptor (wherein the effectiveness may be expressed as moles of substrate converted per time unit or release of second messenger(s) per time unit) and/or (2) the time period during which the enzyme or receptor is active are altered (e.g., mutated or enhanced), thereby increasing the activity of the activating regulator molecules.

The expression "activating mutation" in a molecule (such as a protein or peptide) as used herein means that (i), if the unmutated molecule is an inhibitor, the mutation reduces or abolishes the inhibitory activity of the molecule, or (ii), if the unmutated molecule is an activator, the mutation enhances the activity of the molecule.

The expression "reduced" in connection with a pharmacological property of a compound (e.g., a pharmacological property of a compound of the invention), such as in "reduced activity towards the dopamine receptor" or "reduced sedative and/or antipsychotic effect, preferably means a reduction of the pharmacological property by up to or by at least 10%, by up to or by at least 20%, by up to or by at least 30%, by up to or by at least 40%, by up to or by at least 50%, by up to or by at least 60%, by up to or by at least 70%, by up to or by at least 80%, by up to or by at least 90% or by up to 100%. Preferably, the reduction is compared to a reference compound, such as (R)-mepazine, (±)-mepazine, and/or thioridazine.

The term "leaving group" as used herein refers to a molecular fragment that departs with a pair of electrons in heterolytic bond cleavage. The ability of a leaving group to depart is generally correlated with the pKa of the conjugate acid, with lower pKa being associated with better leaving group ability. Since leaving group ability is a kinetic phenomenon, relating to a reaction's rate, whereas pKa is a thermodynamic phenomenon, describing the position of an equilibrium, the correlation is not perfect. However, it is a general rule that more highly stabilized anions act as better leaving groups. Preferred leaving groups are those which can be easier replaced in a substitution reaction (e.g., LG-R'+Y⁻→Y—R'+LG⁻) than an OH-group in the substitution reaction (e.g., HO—R'+Y⁻→Y—R'+HO⁻) under comparable reaction conditions. Exemplary leaving groups according to the present invention include halogens (i.e., —Cl, —Br, or —I) and sulfonate moieties. Preferred sulfonate moieties have the formula —OS(O)$_2$R, wherein R is F, Cl, alkyl having 1, 2, 3, 4, 5, or 6 carbon atoms, perfluorinated alkyl having 1, 2, 3, 4, 5, or 6 carbon atoms (such as CF$_3$ or nonafluorobutyl), or aryl (e.g., having 6 to 10 carbon atoms, such as phenyl or naphthyl), optionally substituted with 1 to 3 substituents selected from the group consisting of halogens (F, Cl, Br, I), alkyl having 1, 2, 3, 4, 5, or 6 carbon atoms, and nitro. Exemplary leaving groups include —Cl, —Br, —I, 4-toluenesulfonate (tosylate), 4-bromobenzenesulfonate (brosylate), 4-nitrobenzenesulfonate (4-nosylate), 2-nitrobenzenesulfonate (2-nosylate), trifluoromethanesulfonate (triflate), not uorobutanesulfonate (nonaflate), methylsulfonate (mesylate), 2,2,2-trifluoroethanesulfonate (tresylate), and fluorosulfonate. See also M. B. Smith and J. March, "March's advanced organic chemistry: reactions, mechanisms, and structure", 5$^{th}$ edition, John Wiley & Sons, Inc., 2001, in particular pages 445 to 449.

A "chemical base" as used herein is any compound which is capable of receiving one or more protons (Brønsted-Lowry acid-base theory). In one embodiment, the chemical base is non-nucleophilic. This is preferred if the use of a nucleophilic chemical base leads to undesired side reactions (such as inversion at an asymmetric atom causing racemization). The chemical base may be inorganic (e.g., NH$_3$, a metal hydroxide (such as NaOH, KOH), a carbonate salt (such as K$_2$CO$_3$ or Cs$_2$CO$_3$), or NaH) or organic (e.g., an organic amine, such as a cyclic amine (e.g., 1,8-diazabicycloundec-7-ene (DBU)), an aliphatic amine (e.g., a linear or branched amine which may have 1, 2, 3, 4, 5, 6, 7, 8, 9, 10, 11, or 12 carbon atoms and which has at least one primary, secondary or tertiary amine group; examples include trialkylamines (such as triethylamine, trimethylamine)), an alkoxide (such sodium tert-butoxide or potassium tert-butoxide), an amine salt (such as lithium diisopropylamide (LDA) or lithium tetramethylpiperidide (LiTMP)), or a silicon-based amide (such as sodium bis(trimethylsilyl)amide (NaHMDS) or potassium bis(trimethylsilyl)amide (KHMDS))). Preferred organic amines include trialkylamines, wherein the alkyl groups have independently 1, 2, 3, 4, 5, or 6 carbon atoms, such as triethylamine (TEA), N,N-diisopropylethylamine (DIEA), or trimethylamine.

Compounds of the Invention

In a first aspect, the present invention provides 10-{[(3S)-1-methylpiperidin-3-yl]methyl}-10H-phenothiazine (the (S)-enantiomer of mepazine, in the following (S)-mepazine) having the following formula:

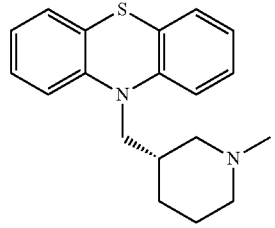 [SMILES: CN1CCC[C@H](CN2c3ccccc3Sc3ccccc32)C1]

It is intended that (S)-mepazine encompasses not only (S)-mepazine as depicted but also its solvates (e.g., hydrates), salts (in particular, pharmaceutically acceptable salts), crystalline forms, non-crystalline forms, amorphous forms, unlabeled forms and isotopically labeled forms.

Since (S)-mepazine contains a basic functionality it may form salts with a variety of inorganic or organic acids. Exemplary inorganic and organic acids as well as exemplary acid addition salts of (S)-mepazine are given in the definition of "pharmaceutically acceptable salt" in the section "Pharmaceutical compositions", below. In a preferred embodiment, the present invention provides (S)-mepazine as its hydrochloride, acetate, or tartrate salt. (S)-Mepazine may be converted into its acid addition salt by conventional means known to the skilled person. The free base form of (S)-mepazine may be regenerated by contacting the salt with a base and isolating the parent compound by using conventional means (e.g., one or more of the following: washing, filtration, liquid chromatography (normal or reverse phase), extraction with two immiscible solvents, concentration under reduced pressure, and recrystallization).

According to the invention, (S)-mepazine can be provided as enantiomerically pure substance. The term "enantiomerically pure" means that (S)-mepazine is essentially free (or is free) of its (R)-enantiomer. For example, enantiomerically pure (S)-mepazine means that (S)-mepazine is present in an enantiomeric ratio (er; S:R) of $\geq 99$, such as $\geq 99.1$, $\geq 99.2$, $\geq 99.3$, $\geq 99.4$, $\geq 99.5$, $\geq 99.6$, $\geq 99.7$, $\geq 99.8$, $\geq 99.9$, $\geq 99.95$, $\geq 99.99$, $\geq 99.995$, or $\geq 99.999$. The expression "(S)-mepazine is free of its (R)-enantiomer" means that in an (S)-mepazine preparation (R)-mepazine is not detectable by conventional means.

Surprisingly, the inventors have found that (S)-mepazine exhibits a much higher binding affinity and inhibitory activity towards MALT1 than (R)-mepazine or (±)-mepazine. In contrast, the enantiomers of thioridazine, i.e., compounds which are structurally very similar to mepazine and which also contain one asymmetric carbon atom (in the piperidinyl ring), do not differ from each other with respect to their binding affinity and inhibitory activity towards MALT1. In one embodiment, the compounds of the invention exhibit additional pharmacological properties (e.g., bioavailability, toxicity, side effects (such as with respect to dopamine D2 receptor antagonism, sedative and/or antipsychotic effects), dosing, patient compliance, compatibility, stability, half-life, etc.), which are in at least one aspect superior to the pharmacological properties exhibited by (R)-mepazine, (±)-mepazine, and/or thioridazine. In one preferred embodiment, the compounds of the invention exhibit reduced activity towards the dopamine D2 receptor (in particular, reduced dopamine D2 receptor antagonism), preferably compared to a reference compound (e.g., (R)-mepazine, (±)-mepazine, and/or thioridazine). It is preferred that the compounds of the invention exhibit reduced sedative and/or antipsychotic effects, e.g., compared to a reference compound (such as (R)-mepazine, (±)-mepazine, and/or thioridazine).

Pharmaceutical Compositions

In a second aspect, the present invention provides a pharmaceutical composition comprising a compound of the first aspect and one or more pharmaceutically acceptable excipients. In one embodiment, the pharmaceutical composition is essentially free (or is free) of (R)-mepazine. For example, a "pharmaceutical composition which is essentially free of (R)-mepazine" means that (S)-mepazine is present in the pharmaceutical composition in an enantiomeric ratio (er; S:R) of $\geq 99$, such as $\geq 99.1$, $\geq 99.2$, $\geq 99.3$, $\geq 99.4$, $\geq 99.5$, $\geq 99.6$, $\geq 99.7$, $\geq 99.8$, $\geq 99.9$, $\geq 99.95$, $\geq 99.99$, $\geq 99.995$, or $\geq 99.999$. The expression that a "pharmaceutical composition is free of (R)-mepazine" means that (R)-mepazine is not detectable in said composition by conventional means.

The pharmaceutical composition may be administered to an individual by any route, such as enterally or parenterally.

The compositions according to the present invention are generally applied in "pharmaceutically acceptable amounts" and in "pharmaceutically acceptable preparations". Such compositions may contain salts, buffers, preserving agents, carriers and optionally other therapeutic agents. "Pharmaceutically acceptable salts" comprise, for example, acid addition salts which may, for example, be formed by mixing a solution of compounds with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compound carries an acidic moiety, suitable pharmaceutically acceptable salts thereof may include alkali metal salts (e.g., sodium or potassium salts); alkaline earth metal salts (e.g., calcium or magnesium salts); and salts formed with suitable organic ligands (e.g., ammonium, quaternary ammonium and amine cations formed using counteranions such as halide, hydroxide, carboxylate, sulfate, phosphate, nitrate, alkyl sulfonate and aryl sulfonate). Illustrative examples of pharmaceutically acceptable salts include, but are not limited to, acetate, adipate, alginate, arginate, ascorbate, aspartate, benzenesulfonate, benzoate, bicarbonate, bisulfate, bitartrate, borate, bromide, butyrate, calcium edetate, camphorate, camphorsulfonate, camsylate, carbonate, chloride, citrate, clavulanate, cyclopentanepropionate, digluconate, dihydrochloride, dodecylsulfate, edetate, edisylate, estolate, esylate, ethanesulfonate, formate, fumarate, galactate, galacturonate, gluceptate, glucoheptonate, gluconate, glutamate, glycerophosphate, glycolylarsanilate, hemisulfate, heptanoate, hexanoate, hexylresorcinate, hydrabamine, hydrobromide, hydrochloride, hydroiodide, 2-hydroxy-ethanesulfonate, hydroxynaphthoate, iodide, isobutyrate, isothionate, lactate, lactobionate, laurate, lauryl sulfate, malate, maleate, malonate, mandelate, mesylate, methanesulfonate, methylsulfate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, 3-phenylpropionate, phosphate/diphosphate, phthalate, picrate, pivalate, polygalacturonate, propionate, salicylate, stearate, sulfate, suberate, succinate, tannate, tartrate, teoclate, tosylate, triethiodide, undecanoate, valerate, and the like (see, for example, Berge et al., *J. Pharm. Sci.*, 66, 1-19 (1977)).

The term "excipient" when used herein is intended to indicate all substances in a pharmaceutical composition which are not active ingredients (e.g., which are therapeutically inactive ingredients that do not exhibit any therapeutic effect in the amount/concentration used), such as, e.g., carriers, binders, lubricants, thickeners, surface active agents, preservatives, emulsifiers, buffers, flavoring agents, colorants, or antioxidants.

The compositions according to the present invention may comprise a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. The "pharmaceutically acceptable carrier" may be in the form of a solid, semisolid, liquid, or combinations thereof. Preferably, the carrier is suitable for enteral (such as oral) or parenteral administration (such as intravenous, intramuscular, subcutaneous, spinal or epidermal administration (e.g., by injection or infusion)). Depending on the route of administration, the active compound, i.e., the compound of the invention, may be coated in a material to protect the compound from the action of acids and other natural conditions that may inactivate the compound.

A composition of the present invention can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Methods for the preparation of such formulations are generally known to those skilled in the art. See, e.g., "Sustained and Controlled Release Drug Delivery Systems", J. R. Robinson, ed., Marcel Dekker, Inc., New York, 1978.

To administer a compound of the invention by certain routes of administration, it may be necessary to coat the compound with, or co-administer the compound with, a material to prevent its inactivation. For example, the compound may be administered to an individual in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., *J. Neuroimmunol.* 1984, 7, 27).

Pharmaceutically acceptable carriers include sterile aqueous solutions or dispersions and sterile powders for the extemporaneous preparation of sterile injectable solutions or dispersions. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Pharmaceutical compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration.

Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the individuals to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For therapeutic formulations, compositions of the present invention include those suitable for enteral administration (such as oral or rectal) or parenteral administration (such as nasal, topical (including vaginal, buccal and sublingual)). The compositions may conveniently be presented in unit dosage form and may be prepared by any methods known in the art of pharmacy. The amount of active ingredient (in particular, the amount of the compound of the present invention) which can be combined with a carrier material to produce a pharmaceutical composition (such as a single dosage form) will vary depending upon the individual being treated, and the particular mode of administration. The amount of active ingredient which can be combined with a carrier material to produce a single dosage form will generally be that amount of the composition which produces a therapeutic effect.

Generally, out of 100% (for the pharmaceutical formulations/compositions), the amount of active ingredient (in particular, the amount of the compound of the present invention, optionally together with other therapeutically active agents, if present in the pharmaceutical formulations/compositions) will range from about 0.01% to about 99%, preferably from about 0.1% to about 70%, most preferably from about 1% to about 30%, wherein the reminder is preferably composed of the one or more pharmaceutically acceptable excipients.

Compositions of the present invention which are suitable for vaginal administration also include pessaries, tampons, creams, gels, pastes, foams or spray formulations containing such carriers as are known in the art to be appropriate. Dosage forms for the topical or transdermal administration of compositions of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The expressions "enteral administration" and "administered enterally" as used herein mean that the drug administered is taken up by the stomach and/or the intestine. Examples of enteral administration include oral and rectal administration. The expressions "parenteral administration" and "administered parenterally" as used herein mean modes of administration other than enteral administration, usually by injection or topical application, and include, without limitation, intravenous, intramuscular, intraarterial, intrathecal, intracapsular, intraosseous, intraorbital, intracardiac, intradermal, intraperitoneal, transtracheal, subcutaneous, subcuticular, intraarticular, subcapsular, intracerebral, intracerebroventricular, subarachnoid, intraspinal, epidural and intrasternal administration (such as by injection and/or infusion) as well as topical administration (e.g., epicutaneous, inhalational, or through mucous membranes (such as buccal, sublingual or vaginal)).

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents, pH buffering agents, and dispersing agents. Prevention of the presence of microorganisms may be ensured both by sterilization procedures, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art (cf., e.g., Remington, "The Science and Practice of Pharmacy", edited by Allen, Loyd V., Jr., 22$^{nd}$ edition, Pharmaceutical Sciences, September 2012; Ansel et al., "Pharmaceutical Dosage Forms and Drug Delivery Systems", 7$^{th}$ edition, Lippincott Williams & Wilkins Publishers, 1999.).

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start with doses of the compounds of the invention employed in the pharmaceutical composition at levels lower than that required in order to achieve the desired therapeutic effect and gradually increase the dosage until the desired effect is achieved. In general, a suitable daily dose of a composition of the invention will be that amount of the compound which is the lowest dose effective to produce a therapeutic effect. Such an effective dose will generally depend upon the factors described above. It is preferred that administration be oral, intravenous, intramuscular, intraperitoneal, or subcutaneous, preferably administered proximal to the site of the target. If desired, the effective daily dose of a therapeutic composition may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical formulation/composition.

In one embodiment, the compounds or compositions of the invention may be administered by infusion, preferably slow continuous infusion over a long period, such as more than 24 hours, in order to reduce toxic side effects. The administration may also be performed by continuous infusion over a period of from 2 to 24 hours, such as of from 2 to 12 hours. Such regimen may be repeated one or more times as necessary, for example, after 6 months or 12 months.

In yet another embodiment, the compounds or compositions of the invention are administered by maintenance therapy, such as, e.g., once a week for a period of 6 months or more.

For oral administration, the pharmaceutical composition of the invention can take the form of, for example, tablets or capsules prepared by conventional means with pharmaceutical acceptable excipients such as binding agents (e.g., pregelatinised maize starch, polyvinylpyrrolidone, hydroxypropyl methylcellulose), fillers (e.g., lactose, microcrystalline cellulose, calcium hydrogen phosphate), lubricants (e.g., magnesium stearate, talc, silica), disintegrants (e.g., potato starch, sodium starch glycolate), or wetting agents (e.g., sodium lauryl sulphate). Liquid preparations for oral administration can be in the form of, for example, solutions, syrups, or suspensions, or can be presented as a dry product for constitution with water or other suitable vehicle before use. Such liquid preparation can be prepared by conventional means with pharmaceutically acceptable additives such as suspending agents (e.g., sorbitol, syrup, cellulose derivatives, hydrogenated edible fats), emulsifying agents (e.g., lecithin, acacia), non-aqueous vehicles (e.g., almond oil, oily esters, ethyl alcohol, fractionated vegetable oils), preservatives (e.g., methyl or propyl-p-hydroxycarbonates, soric acids). The preparations can also contain buffer salts, flavouring, coloring and sweetening agents as deemed appropriate. Preparations for oral administration can be suitably formulated to give controlled release of the pharmaceutical composition of the invention.

The pharmaceutical composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc.

For administration by inhalation, the pharmaceutical composition of the invention is conveniently delivered in the form of an aerosol spray presentation from a pressurised pack or a nebulizer, with the use of a suitable propellant (e.g., dichlorodifluoromethane, trichlorofluoromethane, dichlorotetrafluoroethane, carbon dioxide, nitrogen, or other suitable gas). In the case of a pressurised aerosol, the dosage unit can be determined by providing a valve to deliver a metered amount. Capsules and cartridges of, for example, gelatine, for use in an inhaler or insufflator can be formulated containing a powder mix of the pharmaceutical composition of the invention and a suitable powder base such as lactose or starch.

The pharmaceutical composition of the invention can be formulated for parenteral administration by injection, for example, by bolus injection or continuous infusion. Formulations for injection can be presented in units dosage form (e.g., in phial, in multi-dose container), and with an added preservative. The pharmaceutical composition of the invention can take such forms as suspensions, solutions or emulsions in oily or aqueous vehicles, and can contain formulatory agents such as suspending, stabilizing, or dispersing agents. Alternatively, the agent can be in powder form for constitution with a suitable vehicle (e.g., sterile pyrogen-free water) before use. Typically, compositions for intravenous administration are solutions in sterile isotonic aqueous buffer. Where necessary, the composition can also include a solubilizing agent and a local anesthetic such as lignocaine to ease pain at the site of the injection. Generally, the ingredients are supplied either separately or mixed together in unit dosage form, for example, as a dry lyophilised powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

Therapeutic compositions can be administered with medical devices known in the art. For example, in a preferred embodiment, a therapeutic composition of the invention can be administered with a needleless hypodermic injection device, such as the devices disclosed in U.S. Pat. No. 5,399,163; U.S. Pat. No. 5,383,851; U.S. Pat. No. 5,312,335; U.S. Pat. No. 5,064,413; U.S. Pat. No. 4,941,880; U.S. Pat. No. 4,790,824; or U.S. Pat. No. 4,596,556. Examples of well-known implants and modules useful in the present invention include those described in: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system.

Many other such implants, delivery systems, and modules are known to those skilled in the art. In certain embodiments, the compounds of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. No. 4,522,811; U.S. Pat. No. 5,374,548; and U.S. Pat. No. 5,399,331. The liposomes may comprise one or more moieties which are selectively transported into specific cells or organs, and thus enhance targeted drug delivery (see, e.g., Ranade (1989) *J. Clin. Pharmacol.* 29: 685). Exemplary targeting moieties include folate or biotin (see, e.g., U.S. Pat. No. 5,416,016 to Low et al.); mannosides (Umezawa et al., (1988) *Biochem. Biophys. Res. Commun.* 153: 1038); antibodies (P. G. Bloeman et al. (1995) *FEBS Lett.* 357: 140; M. Owais et al. (1995) *Antimicrob. Agents Chemother.* 39: 180); and surfactant protein A receptor (Briscoe et al. (1995) *Am. J. Physiol.* 1233: 134).

In one embodiment of the invention, the compounds of the invention are formulated in liposomes. In a more preferred embodiment, the liposomes include a targeting moiety. In a most preferred embodiment, the therapeutic compounds in the liposomes are delivered by bolus injection to a site proximal to the desired area, e.g., the site of a tumor (e.g., cancer). The composition must be fluid to the extent that easy syringability exists. It must be stable under the conditions of manufacture and storage and must be preserved against the contaminating action of microorganisms such as bacteria and fungi.

A "therapeutically effective dosage" for tumor therapy (e.g., cancer therapy) can be measured by objective tumor (e.g., cancer) responses which can either be complete or partial. A complete response (CR) is defined as no clinical, radiological or other evidence of disease. A partial response (PR) results from a reduction in aggregate tumor (e.g., cancer) size of greater than 50%. Median time to progression is a measure that characterizes the durability of the objective tumor response.

A "therapeutically effective dosage" for tumor therapy (e.g., cancer therapy) can also be measured by its ability to stabilize the progression of disease. The ability of a compound to inhibit a tumor (e.g., cancer) can be evaluated in an animal model system predictive of efficacy in human tumors (e.g., human cancers). Alternatively, this property of a composition can be evaluated by examining the ability of the compound to inhibit cell growth or apoptosis by in vitro assays known to the skilled practitioner. A therapeutically effective amount of a therapeutic compound can decrease tumor size (e.g., cancer size), or otherwise ameliorate symptoms in an individual. One of ordinary skill in the art would be able to determine such amounts based on such factors as the individual's size, the severity of the individual's symptoms, and the particular composition or route of administration selected.

The composition must be sterile and fluid to the extent that the composition is deliverable by syringe. In addition to water, the carrier can be an isotonic buffered saline solution, ethanol, polyol (for example, glycerol, propylene glycol, and liquid polyetheylene glycol, and the like), and suitable mixtures thereof.

The pharmaceutical composition of the invention can also, if desired, be presented in a pack, or dispenser device which can contain one or more unit dosage forms containing the said agent. The pack can for example comprise metal or plastic foil, such as blister pack. The pack or dispenser device can be accompanied with instruction for administration.

The pharmaceutical composition of the invention can be administered as sole active agent or can be administered in combination with other therapeutically active agents.

Inhibition of Paracaspase Activity and Therapeutic Applications

In further aspects, the present application provides a compound of the first aspect or a pharmaceutical composition of the second aspect for inhibiting a paracaspase and for use in therapy. In one embodiment of theses aspects, enantiomerically pure (S)-mepazine is utilized and/or the pharmaceutical composition is essentially free (or is free) of (R)-mepazine.

It is contemplated that the compound of the first aspect may be used for inhibiting a paracaspase in vitro, such as in an isolated cell, an isolated cell culture, or a sample isolated from a subject.

As demonstrated in the examples below, the compounds of the present invention can be used to treat a disease or disorder which is treatable by an inhibitor of a paracaspase, in particular to treat a cancer that is associated with deregulated, in particular constitutive, proteolytic activity of a paracaspase compared to the state in a healthy individual.

In one embodiment, the paracaspase is MALT1. In a preferred embodiment, the disease or disorder which is treatable by an inhibitor of a paracaspase is a lymphoma, preferably mucosa-associated lymphoid tissue (MALT) lymphoma or diffuse large B-cell lymphoma (DLBCL), such as activated B-cell subtype of diffuse-large B cell lymphoma (ABC-DLBCL). In a preferred embodiment, the disease or disorder which is treatable by an inhibitor of a paracaspase is ABC-DLBCL or MALT lymphoma.

As described herein, diffuse large B-cell lymphoma (DLBCL) is a type of aggressive lymphoma. One major subtype of DLBCL which has been identified based on its genetic activity is the B-cell subtype of diffuse-large B cell lymphoma (ABC-DLBCL). As set forth above, Ferch et al., *Exp. Med.* 2009, 206, 2313-2320 showed that aggressive activated B cell-like (ABC) diffuse large B cell lymphoma (DLBCL) cells possess constitutively assembled CARD11-BCL10-MALT1 (CBM) complexes that continuously and selectively process A20. Moreover, inhibition of MALT1 paracaspase leads to ABC-DLBCL cell death and growth retardation.

MALT lymphoma is a cancer of the B-cell lymphocytes. It usually affects older people who are in their 60s. Most Non-Hodgkin Lymphomas (NHLs) start in the lymph nodes, but MALT lymphoma starts in a type of lymphatic tissue called mucosa-associated lymphoid tissue (MALT). The stomach is the most common area for MALT lymphoma to develop in, but it may also start in other organs such as the lung, thyroid, salivary gland or bowel. MALT lymphomas may start in areas of the body where there has been an infection or when the person has an autoimmune condition affecting that area. Because MALT lymphoma develops outside the lymph nodes, it's also known as extranodal lymphoma. Gastric MALT lymphoma is frequently associated (72-98%) with chronic inflammation as a result of the presence of *Helicobacter pylori* (Parsonnet J. (1994). *New Engl. J. Med.* 330 (18): 1267-71). The initial diagnosis is made by biopsy of suspicious lesions on esophagogastroduodenoscopy (EGD, upper endoscopy). Simultaneous tests for *H. pylori* are also done to detect the presence of this microbe. In other sites, chronic immune stimulation is also suspected in the pathogenesis (e.g. association between chronic autoimmune diseases such as Sjögren's syndrome and Hashimoto's thyroiditis, and MALT lymphoma of the salivary gland and the thyroid). In MALT lymphoma the frequent translocation t(11;18)(q21;q21) creates a fusion between the C-terminus of MALT1 including the paracaspase domain and the N-terminus of IAP2. The paracaspase domain of IAP2-MALT1 fusion protein catalyzes the cleavage of NIK and thereby enhances non-canonical NF-κB activation, which confers apoptosis resistance (Rosebeck et al., *Science* 2011, 331, 468-472; Isaacson and Du, *Nat. Rev. Cancer* 2004, 4, 644-53). Two further translocations have been identified: t(1;14)(p22;q32) which deregulates BCL10, and t(14;18)(q32;q21), which deregulates MALT1. All three translocations are believed to turn-on the same pathway, i.e. the pathway of API2-MALT.

Therefore, the examples herein below indicate that with respect to inhibition of MALT1 and, thus, to the treatment of MALT lymphoma and ABC-DLBCL, (S)-mepazine is much more effective than its (R)-enantiomer or the structurally very similar enantiomers of thioridazine.

Thus, the present invention provides (i) a compound of the invention (or a pharmaceutical composition comprising such compound optionally together with a pharmaceutically acceptable excipient) for use in a method of treating any disease or disorder which is treatable by an inhibitor of a paracaspase in an individual and (ii) a method of treating a disease or disorder which is treatable by an inhibitor of a paracaspase in an individual, comprising administering a pharmaceutically effective amount of a compound of the invention (or a pharmaceutical composition comprising such compound optionally together with a pharmaceutically acceptable excipient) to the individual. In this regard, the disease or disorder which is treatable by an inhibitor of a paracaspase is preferably cancer, more preferably a cancer that is associated with deregulated (in particular constitutive) proteolytic activity of a paracaspase compared to the state in a healthy individual. Preferably, the disease or disorder which is treatable by an inhibitor of a paracaspase is a lymphoma, preferably an extranodal lymphoma, such as a stomach, thyroid, salivary gland or bowel lymphoma. Most preferably, the disease or disorder which is treatable by an inhibitor of a paracaspase is the activated B-cell subtype of diffuse-large B cell lymphoma or MALT lymphoma. Moreover, the individual is preferably a mammal and more preferably a human. The compounds of the invention (or the pharmaceutical composition comprising such compound) may be administered to the individual by any route, preferably by any route described above in section "Pharmaceutical compositions" for the administration of the pharmaceutical composition of the invention.

In addition, proteolytic activity of MALT1 is required for an optimal activation of an adaptive immune response. Pharmacological inhibition using the antagonistic peptide z-VRPR-FMK or genetic destruction of MALT1 protease activity prevents a full NT-κB transcriptional response and IL-2 production in CD4 T cells, revealing that MALT1 protease activity is essential for optimal T cell activation (Duwel et al., *J. Immunol.* 2009, 182, 7718-7728). Further, the non-competitive small molecule MALT1 inhibitors thioridazine and mepazine also impair full IL-2 production in response to TCR/CD28 stimulation in primary T cells (Nagel et al., *Cancer cell* 2012, 22, 825-837). MALT1 protease activity does not directly enhance TCR/CD28 triggered canonical IKK/NF-κB activation (Rebeaud et al., *Nat. Immunol.* 2008, 9, 272-28; Duwel et al., *J Immunol.* 2009, 182, 7718-7728), but MALT1 proteolytic activity warrants a robust and prolonged response. The requirement of MALT1 cleavage activity at later stages of T cell activation, differentiation and effector functions is supported by the MALT1 substrates BCL10, A20, CYLD, RelB and Regnase-1. Substrates cleavage demonstrates that the unique cleavage activity of MALT1 contributes to optimal T cell function by inactivating multiple negative regulators that are influencing diverse cellular processes ranging from signaling, transcription, mRNA stability to cell adhesion (Coornaert et al., *Nat. Immunol.* 2008, 9, 263-271; Rebeaud et al., *Nat. Immunol.* 2008, 9, 272-28; Duwel et al., *J Immunol.* 2009, 182, 7718-7728; Hailfinger et al., *PNAS USA* 2011, 108, 14596-14601; Staal et al., *EMBO J.* 2011, 30, 1742-1752; Uehata et al., *Cell* 2013, 153, 1036-1049). Thus, the inhibitory action of the MALT1 inhibitory compounds of the invention on T cell activation indicates a potential medical use as immunosuppressant, for instance in the treatment of allergy and asthma. Furthermore, it has recently been demonstrated that MALT1 protease activity contributes to T cell activation, differentiation and effector function and, thus, the onset and the clinical score in murine experimental autoimmune encephalomyelitis (EAE), which is the main animal model for multiple sclerosis (MS); cf. Baxter, *Nat. Rev. Immunol.* 2007, 7, 904-912; Mc Guire et al., *J. Immunol.* 2013, 190, 2896-2903; Brüstle et al., *J. Clin. Invest.* 2012, 122, 4698-4709.

Accordingly, also encompassed by the present invention is (i) a compound of the invention (or a pharmaceutical composition comprising such compound optionally together with a pharmaceutically acceptable excipient) for use in a method of treatment of paracaspase-dependent immune diseases and (ii) a method of treating a paracaspase-dependent immune disease in an individual, comprising administering a pharmaceutically effective amount of a compound of the invention (or a pharmaceutical composition comprising such compound optionally together with a pharmaceutically acceptable excipient) to the individual. In this regard, the paracaspase-dependent immune disease is preferably an allergic inflammation. In a preferred embodiment, the paracaspase is MALT1. The paracaspase-dependent immune disease may also be a T-cell driven disease where the T-cell responses are counteracted by the compounds of the invention. In this regard the paracaspase-dependent immune disease can be hypersensitivity of the immune system or a chronic inflammation such as allergy (as mentioned) or asthma. Further, the paracaspase-dependent immune disease can be an autoimmune disease, which includes but is not limited to diseases such as Sjögren's syndrome, Hashimoto's thyroiditis, multiple sclerosis, inflammatory bowel diseases (e.g. Crohn's disease, ulcerative colitis), lupus erythematosus, psoriasis, chronic obstructive pulmonary disease, rheumatoid arthritis or psoriatic arthritis. Moreover, the individual is preferably a mammal and more preferably a human. The compounds of the invention (or the pharmaceutical composition comprising such compound) may be administered to the individual by any route, preferably by any route described above in section "Pharmaceutical compositions" for the administration of the pharmaceutical composition of the invention.

Processes of Preparation

In a sixth aspect, the present invention provides a process for the preparation of a compound of the first aspect, comprising the step of reacting phenothiazine with a piperidine derivative of formula (3)

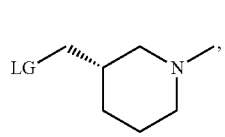

(3)

wherein LG is a leaving group. The leaving group LG may be selected from the group consisting of —Cl, —Br, —I, and a sulfonate moiety. Preferably, the sulfonate moiety is selected from the group consisting of 4-toluenesulfonate (tosylate), 4-bromobenzenesulfonate (brosylate), 4-nitrobenzenesulfonate (4-nosylate), 2-nitrobenzenesulfonate (2-nosylate), trifluoromethanesulfonate (triflate), nonafluorobutanesulfonate (nonaflate), methylsulfonate (mesylate), 2,2,2-trifluoroethanesulfonate (tresylate), and fluorosulfonate. In one embodiment, the leaving group LG is —Cl, —Br, mesylate, triflate, or tosylate, preferably tosylate. In any of the above embodiments, the step of reacting phenothiazine with the piperidine derivative of formula (3) may be conducted in the presence of a chemical base, such as NaH. In any of the above embodiments, the step of reacting phenothiazine with the piperidine derivative of formula (3) may be conducted in a solvent, preferably an organic solvent in which phenothiazine is soluble (e.g., dimethylformamide (DMF)). For example, the phenothiazine may be dissolved in a solvent, the chemical base is added (preferably in an amount to deprotonate the phenothiazine, such as an amount of chemical base in excess to the amount of the phenothiazine used (e.g., the molar ratio of chemical base to phenothiazine may be 1.1-4.0:1, such as 2.0-3.0:1)), and then the piperidine derivative of formula (3), preferably as a solution in a solvent (e.g., the same solvent as that utilized to dissolve the phenothiazine), is added to produce the compound of the first aspect.

In any of the above embodiments, the process of the sixth aspect may further comprise the step of isolating and/or purifying the compound of the first aspect. The step of isolating and/or purifying the compound of the first aspect may be conducted by conventional means, such as one or more of the following: washing, filtration, liquid chromatography (normal or reverse phase), extraction with two immiscible solvents, concentration under reduced pressure, and recrystallization. If it is desired to provide (S)-mepazine as a particular salt (such as hydrochloride), (S)-mepazine may be solved in an appropriate solvent (such as ethanol), the desired acid (such as HCl) is added, and the desired (S)-mepazine salt may be isolated and/or purified by conventional means.

In any of the above embodiments, the process of the sixth aspect may further comprise the step of converting the tertiary amine of formula (2)

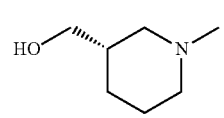

(2)

into the piperidine derivative of formula (3). Reagents and reaction conditions for the conversion of an alcohol group into a leaving group are known to the skilled person (cf., e.g., M. B. Smith and J. March, "March's advanced organic chemistry: reactions, mechanisms, and structure", 5th edition, John Wiley & Sons, Inc., 2001, in particular pages 445 to 449, 518, 519, and 576). For example, if in one embodiment the leaving group LG in the piperidine derivative of formula (3) is to be a sulfonate moiety, the tertiary amine of formula (2) may be reacted with an appropriate sulfonyl chloride compound (e.g., RS(O)$_2$Cl, wherein R is F, Cl, alkyl having 1, 2, 3, 4, 5, or 6 carbon atoms (optionally substituted with 1, 2, or 3 atoms independently selected from F and Cl), perfluorinated alkyl having 1, 2, 3, 4, 5, or 6 carbon atoms (such as CF$_3$ or nonafluorobutyl), or aryl (e.g., having 6 to 10 carbon atoms, such as phenyl or naphthyl), optionally substituted with 1 to 3 substituents selected from the group consisting of halogens (F, Cl, Br, I), alkyl having 1, 2, 3, 4, 5, or 6 carbon atoms, and nitro). In any of the above embodiments, the step of converting the tertiary amine of formula (2) into the piperidine derivative of formula (3) may be conducted in the presence of a chemical base, such as an organic amine (e.g., triethylamine). In case the leaving group LG in the piperidine derivative of formula (3) is to be a sulfonate moiety, the conversion of the tertiary amine of formula (2) into the piperidine derivative of formula (3) may be conducted in the presence of an esterification catalyst (e.g., dimethylaminopyridine). In any of the above embodiments, the conversion may be conducted in a solvent, e.g., an organic solvent in which the tertiary amine of formula (2) is soluble (for example, dichloromethane), preferably at an initial temperature below room temperature (e.g., starting at 0° C. and gradually warming to room temperature over a period of 12 to 24 hours). In any of the above embodiments the piperidine derivative of formula (3) may be isolated and/or purified by conventional means (such as one or more of the following: washing, filtration, liquid chromatography (normal or reverse phase), extraction with two immiscible solvents, concentration under reduced pressure, and recrystallization), before reacting it with phenothiazine to provide (S)-mepazine.

In any of the above embodiments, the process of the sixth aspect may further comprise the step of converting a carbamate of formula (1)

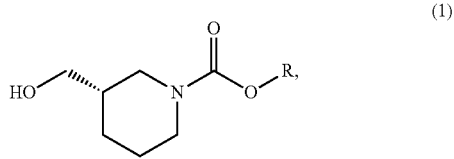

(1)

wherein R is an optionally substituted alkyl, cycloalkyl, heterocyclyl, aryl, or heteroaryl group, into the tertiary amine of formula (2).

Reagents and reaction conditions for the conversion of a carbamate group (such as R'R"NC(O)OR) into a tertiary amine (such as R'R"NCH$_3$) are known to the skilled person. In one embodiment, the conversion of the carbamate of formula (1) into the amine of formula (2) may be conducted by removing the C(O)OR group from the carbamate of formula (1) and selectively methylating the nitrogen atom (optionally the alcohol group is protected before the methylation takes place and is removed thereafter); cf., e.g., M. B. Smith and J. March, "March's advanced organic chemistry: reactions, mechanisms, and structure", 5$^{th}$ edition, John Wiley & Sons, Inc., 2001, in particular pages 499 to 501 and 504. In an alternative embodiment, the conversion of the carbamate of formula (1) into the tertiary amine of formula (2) may be conducted in the presence of a reducing agent, such as LiAlH$_4$.

In any of the above embodiments, the conversion may be conducted in a solvent (e.g., an organic solvent in which the carbamate of formula (1) is soluble, for example, tetrahydrofuran (THY)), preferably at an initial temperature below room temperature (e.g., starting at 0° C. and gradually warming to room temperature over a period of 12 to 24 hours). In one embodiment, after completion of the conversion, the reaction mixture is cooled below room temperature (e.g., to a temperature of 0° C.), and then water, a chemical base (e.g., an inorganic base, such as NaOH), and again water are added (according to Fieser, "Reagents for Organic Synthesis", Wiley (1967), 581-595). The tertiary amine of formula (2) may be isolated and/or purified by conventional means (such as one or more of the following: washing, filtration, liquid chromatography (normal or reverse phase), extraction with two immiscible solvents, concentration under reduced pressure, and recrystallization), before converting it into the piperidine derivative of formula (3).

In any of the above embodiments, the group R preferably is C$_{1-10}$ alkyl (e.g., methyl, ethyl, propyl (such as isopropyl), butyl (such as tert-butyl), pentyl, hexyl), C$_{3-10}$ cycloalkyl (e.g., cyclopropyl, cyclopentyl, cyclohexyl, or cycloheptyl), 3- to 10-membered heterocyclyl (e.g., 5- or 6-membered heterocyclyl, such as morpholino, pyrrolidinyl, imidazolidinyl, pyrazolidinyl, piperidinyl, piperazinyl, di- and tetrahydrofuranyl, di- and tetrahydrothienyl), C$_{3-14}$ aryl (e.g., phenyl or naphthyl), or 3- to 14-membered heteroaryl (e.g., 5- or 6-membered heteroaryl, such as furanyl, thienyl, pyrrolyl, imidazolyl, pyrazolyl, pyridyl, or pyrimidinyl), wherein each of the alkyl, cycloalkyl, heterocyclyl, aryl, and heteroaryl groups may be unsubstituted or substituted with one or more (e.g., 1, 2, 3, 4, or 5, such as 1, 2, or 3) individually selected 1$^{st}$ level substituents (such as C$_{1-4}$ alkyl, C$_{2-4}$ alkenyl, C$_{2-4}$ alkynyl, 5- or 6-membered aryl, 5- or 6-membered heteroaryl, 3- to 7-membered cycloalkyl, 3- to 7-membered heterocyclyl, halogen, —CF$_3$, —CN, azido, —NO$_2$, —OH, —O(C$_{1-3}$ alkyl), —S(C$_{1-3}$ alkyl), —NH$_2$, —NH(C$_{1-3}$ alkyl), —N(C$_{1-3}$ alkyl)$_2$, —NHS(O)$_2$(C$_{1-3}$ alkyl), —S(O)$_2$NH$_{2-z}$(C$_{1-3}$ alkyl)$_z$, —C(=O)OH, —C(=O)O(C$_{1-3}$ alkyl), —C(=O)NH$_{2-z}$(C$_{1-3}$ alkyl)$_z$, —NHC(=O)(C$_{1-3}$ alkyl), —NHC(=NH)NH$_{z-2}$(C$_{1-3}$ alkyl)$_z$, and —N(C$_{1-3}$ alkyl)C(=NH)NH$_{2-z}$(C$_{1-3}$ alkyl), wherein z is 0, 1, or 2 and C$_{1-3}$ alkyl is methyl, ethyl, propyl or isopropyl, wherein each of the alkyl, alkenyl, alkynyl, cycloalkyl, aryl, heteroaryl, and heterocyclyl 1$^{st}$ level substituent groups is optionally substituted with one, two or three 2$^{nd}$ level substituents). Exemplary, R groups include straight chained or branched chained alkyl having 1, 2, 3, 4, 5, or 6 carbon atoms (such as tert-butyl), cycloalkyl having 3, 5, 6, or 7 ring carbon atoms (such as hexyl), and aryl having 6 or 10 ring carbon atoms (such as phenyl), wherein each of the alkyl, cycloalkyl, and aryl groups is optionally substituted with one, two or three substituents individually selected from the group consisting of C$_{1-4}$ alkyl, 6-membered aryl, 5- or 6-membered heteroaryl, 3- to 7-membered cycloalkyl, 3- to 7-membered heterocyclyl, halogen, —CF$_3$, —CN, azido, —NO$_2$, —OH, —O(C$_{1-3}$ alkyl), —S(C$_{1-3}$ alkyl), —NH$_2$, —NH(C$_{1-3}$ alkyl), —N(C$_{1-3}$ alkyl)$_2$, —NHS(O)$_2$(C$_{1-3}$ alkyl), —S(O)$_2$NH$_{2-z}$(C$_{1-3}$ alkyl)$_z$, —C(=O)OH, —C(=O)O(C$_{1-3}$ alkyl), —C(=O)NH$_{2-z}$(C$_{1-3}$ alkyl), and —NHC(=O)(C$_{1-3}$ alkyl)$_z$, wherein z is 0, 1, or 2 and C$_{1-3}$ alkyl is methyl, ethyl, propyl or isopropyl (preferably, the one, two or three substituents are individually selected from the group consisting of C$_{1-3}$ alkyl, halogen, —CF$_3$, —OH, —OCH$_3$, —SCH$_3$, —NH$_{2-z}$(C$_3$)$_z$, —C(=O)OH, and —C(=O)OCH$_3$, wherein z is 0, 1, or 2).

In one embodiment the process of the sixth aspect comprises the steps of (i) converting a tertiary amine of formula (2) into a piperidine derivative of formula (3) and then (ii) reacting phenothiazine with the piperidine derivative of formula (3), wherein steps (i) and (ii) are as described above. In another embodiment, the process of the sixth aspect comprises the steps of (1) converting a carbamate of formula (1) into a tertiary amine of formula (2), then (ii) converting the tertiary amine of formula (2) into a piperidine derivative of formula (3), and then (iii) reacting phenothiazine with the piperidine derivative of formula (3), wherein steps (i) to (iii) are as described above.

In a seventh aspect, the present invention provides a process for the preparation of a tertiary amine of formula (2)

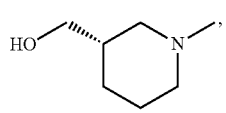

(2)

the method comprising the step of reacting a carbamate of formula (1)

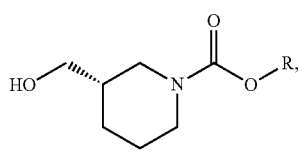

(1)

wherein R is an optionally substituted alkyl, cycloalkyl, heterocyclyl, aryl, or heteroaryl group, with a reducing agent, such as LiAlH$_4$. Preferably, the group R is C$_{1-10}$ alkyl (e.g., methyl, ethyl, propyl (such as iso-propyl), butyl (such as tert-butyl), pentyl, hexyl), C$_{3-10}$ cycloalkyl (e.g., cyclopropyl, cyclopentyl, cyclohexyl, or cycloheptyl), 3- to 10-membered heterocyclyl (e.g., 5- or 6-membered heterocyclyl, such as morpholino, pyrrolidinyl, imidazolidinyl, pyrazolidinyl, piperidinyl, piperazinyl, di- and tetrahydrofuranyl, di- and tetrahydrothienyl), C$_{3-14}$ aryl (e.g., phenyl or naphthyl), or 3- to 14-membered heteroaryl (e.g., 5- or 6-membered heteroaryl, such as furanyl, thienyl, pyrrolyl, imidazolyl, pyrazolyl, pyridyl, or pyrimidinyl), wherein each of the alkyl, cycloalkyl, heterocyclyl, aryl, and heteroaryl groups may be unsubstituted or substituted with one or more (e.g., 1, 2, 3, 4, or 5, such as 1, 2, or 3) individually selected 1$^{st}$ level substituents (such as C$_{1-4}$ alkyl, C$_{2-4}$ alkenyl, C$_{2-4}$ alkynyl, 5- or 6-membered aryl, 5- or 6-membered heteroaryl, 3- to 7-membered cycloalkyl, 3- to 7-membered heterocyclyl, halogen, —CF$_3$, —CN, azido, —NO$_2$, —OH, —O(C$_{1-3}$ alkyl), —S(C$_{1-3}$ alkyl), —NH$_2$, —NH(C$_{1-3}$ alkyl), —N(C$_{1-3}$ alkyl)$_2$, —NHS(O)$_2$(C$_{1-3}$ alkyl), —S(O)$_2$NH$_{2-z}$(C$_{1-3}$ alkyl)$_z$, —C(=O)OH, —C(=O)O(C$_{1-3}$ alkyl), —C(=O)NH$_{2-z}$(C$_{1-3}$ alkyl)$_z$, —NHC(=O)(C$_{1-3}$ alkyl), —NHC(=NH)NH$_{2-z}$(C$_{1-3}$ alkyl)$_z$, and —N(C$_{1-3}$ alkyl)C(=NH)NH$_{2-z}$(C$_{1-3}$ alkyl)$_z$, wherein z is 0, 1, or 2 and C$_{1-3}$ alkyl is methyl, ethyl, propyl or isopropyl, wherein each of the alkyl, alkenyl, alkynyl, cycloalkyl, aryl, heteroaryl, and heterocyclyl 1$^{st}$ level substituent groups is optionally substituted with one, two or three 2$^{nd}$ level substituents). Exemplary, R groups include straight chained or branched chained alkyl having 1, 2, 3, 4, 5, or 6 carbon atoms (such as tert-butyl), cycloalkyl having 3, 5, 6, or 7 ring carbon atoms (such as hexyl), and aryl having 6 or 10 ring carbon atoms (such as phenyl), wherein each of the alkyl, cycloalkyl, and aryl groups is optionally substituted with one, two or three substituents individually selected from the group consisting of C$_{1-4}$ alkyl, 6-membered aryl, 5- or 6-membered heteroaryl, 3- to 7-membered cycloalkyl, 3- to 7-membered heterocyclyl, halogen, —CF$_3$, —CN, azido, —NO$_2$, —OH, —O(C$_{1-3}$ alkyl), —S(C$_{1-3}$ alkyl), —NH$_2$, —NH(C$_{1-3}$ alkyl), —N(C$_{1-3}$ alkyl)$_2$, —NHS(O)$_2$(C$_{1-3}$ alkyl), —S(O)$_2$NH$_{2-z}$(C$_{1-3}$ alkyl)$_z$, —C(=O)OH, —C(=O)O(C$_{1-3}$ alkyl), —C(=O)NH$_{2-z}$(C$_{1-3}$ alkyl)$_z$, and —NHC(=O)(C$_{1-3}$ alkyl), wherein z is 0, 1, or 2 and C$_{1-3}$ alkyl is methyl, ethyl, propyl or isopropyl (preferably, the one, two or three substituents are individually selected from the group consisting of C$_{1-3}$ alkyl, halogen, —CF$_3$, —OH, —OCH$_3$, —SCH$_3$, —NH$_{2-z}$(CH$_3$)$_z$, —C(=O)OH, and —C(=O)OCH$_3$, wherein z is 0, 1, or 2).

In any of the above embodiments, the reaction of the carbamate of formula (1) with a reducing agent may be conducted in a solvent, e.g., an organic solvent in which the carbamate of formula (1) is soluble (for example, tetrahydrofuran (THF)), preferably at an initial temperature below room temperature (e.g., starting at 0° C. and gradually warming to room temperature over a period of 12 to 24 hours). In one embodiment, after completion of the reaction, the reaction mixture is cooled below room temperature (e.g., to a temperature of 0° C.), and then water, a chemical base (e.g., an inorganic base, such as NaOH), and again water are added (according to Fieser, "Reagents for Organic Synthesis", Wiley (1967), 581-595). The tertiary amine of formula (2) may be isolated and/or purified by conventional means (such as one or more of the following: washing, filtration, liquid chromatography (normal or reversed phase), extraction with two immiscible solvents, concentration under reduced pressure, and recrystallization).

If it is desired to prepare the compounds of the invention (or one of its intermediates, i.e., the tertiary amine of formula (2)) in an isotopically labeled form, one or more isotopically labeled starting materials (e.g., an isotopically labeled carbamate of formula (1), an isotopically labeled tertiary amine of formula (2), an isotopically labeled piperidine derivative of formula (3), and/or an isotopically labeled phenothiazine) can be used in the processes of the present invention.

The compounds of the present invention were prepared as described above and in Examples below, or prepared by methods analogous thereto, which are readily known and available to one of ordinary skill in the art of organic synthesis (see, for example, H. Ulrich "Phenothiazines" in "Methods of Organic Chemistry", Houben-Weyl, Georg Thieme Verlag, Stuttgart, 510-556).

The invention is illustrated by the following examples which are not to be construed to limit the present invention in any way. Those examples which are not covered by the claims are given for comparative purposes only.

EXAMPLES

Abbreviations

DCM: dichloromethane
DIEA: N,N-diisopropylethylamine
DMF: N,N-dimethylformamide
DMSO: dimethylsulfoxide
DTT: dithiothreitol
Flash Chromatography: as described by Still, W. C., et al., *J. Org. Chem.* 1978, 43, 2923.

h: hour(s)
min: minute(s)
TFA: trifluoroacetic acid
THF: tetrahydrofuran

Experimental Procedures

Cloning, Expression and Purification

For crystallization and tryptophan fluorescence quenching human MALT1 (L339-R719) was used. Protein expression was performed in *Escherichia coli* Rosetta™ (DE3) strain (Novagen). Cells were resuspended in lysis buffer (50 mM Hepes pH 7.5, 300 mM NaCl, 7 mM imidazole and 4 mM β-mercaptoethanol), lysed by sonication and clarified by centrifugation. Proteins were further purified by Ni-NTA affinity chromatography (Qiagen) and size exclusion chromatography (S200 26/60, GE-Healthcare). Monomeric and ligand free dimeric MALT1 elute as single peak in size-exclusion-buffer (25 mM Hepes pH 7.5, 300 mM NaCl, 5 mM DTT) and were concentrated to 8 mg/ml.

For the enzymatic cleavage assay GST tagged $MALT1_{325-760}$ was expressed in BL21 RIL *E. coli* strain (Novagen) for 16 hr at 18° C. Cells were harvested and lysed by sonication in lysis buffer (50 mM Hepes, pH 7.5, 10% glycerol, 0.1% [vol/vol] Triton X-100, 1 mM DTT, 150 mM NaCl, 2 mM $MgCl_2$, incl. protease inhibitors). MALT1 was purified via an ÄKTA™ liquid chromatography system using Glutathione FastTrap columns (GE Healthcare).

Tryptophan Fluorescence Quenching Assay

Fluorescence quenching of tryptophan W580 was measured with the fluorescence spectrometer (FluoroMax-P, HORIBA Jobin Yvon) at an extinction wavelength of 285 nm and an emission wavelength of 329 nm. The measurement was performed by 2 µl titration steps of 400 µM, 800 µM, 4 mM, 8 mM thioridazine and mepazine stock solutions in $H_2O$ against 0.5 µM monomeric MALT1 (L339-R719) in 1.6 ml assay buffer (5 mM Hepes pH 7.0, 300 mM NaCl) at 20° C. The quenching assay of thioridazine and mepazine enantiomers was performed equally to racemates measurements. CD-spectroscopy measurements (CD-Spektrometer Jasco J 810, JASCO GmbH) were performed with a 200 µl reaction mix of 2.2 µM monomeric with a final concentration of 0.1 mM, 0.25 mM and 0.5 mM thioridazine in assay buffer for 2 min at 20° C.

MALT1 Paracaspase Activity Assay

For the cleavage assay 20 ng of $GST-MALT1_{325-760}$ and compounds or DMSO were pre-incubated in 384-well non-binding microplates and then 50 µM of Ac-LRSR-AMC substrate was added. Following 30 min of incubation at 30° C., the fluorescence of the cleaved AMC was measured for 1 h using a Synergy 2 Microplate Reader (Biotek). Protease activity was expressed in relative fluorescence units, where DMSO treated controls were set to 100% and fluorescence of compound-treated wells was calculated appropriately. The $IC_{50}$ of the inhibition was calculated using PRISM 5 (GraphPad) and curves show the mean of at least three independent experiments with SD indicated. Mepazine, thioridazine, and the respective enantiomers were dissolved in DMSO. Controls were treated with appropriate amounts of the solvents.

Crystallization

Thioridazine bound crystals were produced by soaking of ligand free dimeric MALT1 crystals (Wiesmann et al. (2012), *J. Mol. Biol.*, 419, 4-21) with 1.5 mM thioridazine in reservoir solution (200 mM magnesium formate, 13% PEG3350). All Crystals were cryoprotected with 15% 2,3-butandiol in reservoir solution and flash frozen with liquid nitrogen.

X-Ray Data Collection, Structure Determination and Refinement

Data collection of thioridazine bound crystals was performed at the ID29 beamline (European Synchrotron Radiation Facility, Grenoble) at a wavelength of 0.972390 Å, also equipped with a PILATUS 6M pixel detector (DECTRIS). Additionally, a second data set of the same crystal at a wavelength of 1.90 Å was collected. All data were processed by using XDS (Kabsch (1993), *J. Appl. Cryst.* 21, 916-24). The model was refined with Phenix (Adams et al. (2010), *Acta Crystallogr. D Biol. Crystallogr.* 66, 213-21). Structure determination of thioridazine bound to MALT1 was solved by molecular replacement with PHASER (McCoy et al. (2007), *J. Appl. Crystallogr.* 40, 658-674) using the ligand free MALT1 (pdb entry: 3V55) as search model. The structure of thioridazine bound MALT1 was resolved at 2.7 Å by iterative AutoBuster (Global Phasing, Cambridge) refinement and model building steps in Coot (Emsley et al. (2010), *Acta Crystallogr. D Biol. Crystallogr.* 66, 486-501). All figures were generated in PyMol (Schrodinger, LLC. The PyMOL Molecular Graphics System, Version 1.3r1. (2010)).

Solvents and Reagents

All chemicals and solvents were purchased from VWR or Sigma Aldrich and used as supplied.

Reaction Handling

All non-aqueous reactions were performed under an atmosphere of nitrogen unless otherwise stated. Column chromatography was performed as described using commercial grade BDH 60 Å, 40-60 µm silica gel (Still et al., *Org. Chem.* 1978, 43, 2923-2925).

NMR Spectroscopy

NMR data was recorded on Bruker Avance (400 MHz) or Bruker Fourier (300 MHz) spectrometers. Measurements were carried out at room temperature. The data is reported as (s=singlet, d=doublet, t=triple, m=multiplet or unresolved, br=broad signal, coupling constant(s) in Hz, integration).

Mass Spectrometry

Mass spectrometric analyses were performed using a Micromass ZMD Electrospray spectrometer equipped with a Waters 2795 Separation Module and Water 996 Photodiode Array Detector.

Analytical HPLC

Analytical HPLC analyses were performed using a Zorbax Eclipse XDB-C18 4.6×50 mm (1.8 µm packing) column using the following method: solvent A—water (0.1% TFA), solvent B—acetonitrile (0.07% TFA) 6 min gradient from 5 to 95% B; 1 min hold; then recycle.

Chiral HPLC

Enantiomeric purity of the thioridazine and mepazine enantiomers was determined by comparison to commercially available racemates using a ChiralPak IA 250×4.6 mm (L×I.D.) amylase tris(3,5-dimethylphenylcarbamate) column. For thioridazine an isocratic gradient of 1% ethanol in hexane containing 0.1% diethylamine modifier was used. In the case of mepazine an isocratic gradient of 1% isopropanol in hexane containing 0.1% diethylamine modifier was used. Both were run at 1 ml/min.

DLBCL Xenograft Model

Tumors were engrafted in 6- to 8-week-old female NOD.Cg-Prkdc$^{scid}$ Il2rg$^{tm1Wjl}$/SzJ (NSG) mice by subcutaneous injection of 4×10$^6$ tumor cells (OCI-Ly10 or Su-DHL-6) resuspended in matrigel (BD). Both tumors were engrafted simultaneously on opposite flanks of individual mice, with four mice for each treatment group. Intraperitoneal injection (IP) of solvent or (S)-mepazine (one injection per day) was started 13 days after transplantation and given continuously every 24 hour thereafter. A daily application of 150 or 300 µg of compound per animal (~25 g) was used, corresponding to approximately 6 or 12 mg/kg, respectively. The tumor size was measured every other day after visual appearance using a caliper and calculated as square millimeters (length×width). Mice were sacrificed when the tumors were above 250 mm$^2$ and statistical data was analyzed with a two-way ANOVA test.

Chronic Progressive EAE (Experimental Allergic Encephalomyelitis) Model

For the EAE model first 1 mg/ml MOG$_{35-55}$ peptides (MOG: myelin/oligodendrocyte glycoprotein; accession no. AAF74786) were emulsified 1:1 in Complete Freund's Adjuvant (CFA, incl. 5 mg/ml heat-killed *M. tuberculum* H37RA). On day one female C57Bl/6 mice (8-10 weeks old) were subcutaneously treated with 0.1 ml of MOG/CFA (0.1 mg MOG/0.25 mg CFA per mouse) in both flanks. In addition 0.2 ml pertussis toxin (1 mg in 1 ml PBS) was intraperitoneally injected immediately after (200 ng per mouse), followed by a second injection the day after. On day 10 mice are randomly distributed among 3 groups with 10 mice per group and an average clinical score of 1 and the IP treatment of the mice with PBS, 16 mg/kg (S)-mepazine (two injections per day, each 8 mg/kg) was started. The clinical score of the mice was determined according to the following parameters: Score 0=no obvious signs of motor dysfunction in mice compared to non-immunized control; 0.5—distal tail limpness; 1=limp or floppy tail; 2=limp tail and weakness in hind legs; 3=limp tail and complete paralysis of hind legs OR limp tail with paralysis of one front and one hind leg; 4=limp tail, complete hind leg and partial front leg paralysis; 5=complete hind and complete front leg paralysis, no movement around cage OR mouse is spontaneously rolling in cage OR mouse found dead due to paralysis.

At the end of the study mice were euthanized and blood serum and also the brain and the spinal cord was collected for a histopathology analysis. Here foci of inflammatory cell infiltrate (at least 50 µm) into the spinal cord were counted and scored using the following criteria: 0=normal; 0.5 very minimal; 1=minimal, 2-4 generally less than 100 µm width/length; 2=mild, 5-7 small discreet foci; 3=moderate, 8-10 small plus larger coalescing areas; 4=marked, 11-13 small plus larger coalescing areas; 5=severe, often multiple coalescing >13. Percent area of white matter that bad demyelination, edema, dilated axons was estimated and used to determine a score using the following criteria: 0=normal; 1=minimal, 1-5% of total are affected; 2=mild, 5-25% of total area affected; 3=moderate, 26-50% of total area affected; 4=marked, 51-75% of total area affected; 5=>75% of total area affected.

CIA (Collagen Induced Arthritis) Model

For the CIA model first the immunogen was prepared by emulsifying a 1:1 (vol:vol) combination of collagen solution (4 mg/ml in 0.01 M acetic acid) and Complete Freund's Adjuvant (CFA incl. heat killed *M. tuberculosis* H37RA 4 mg/ml). On Day 0 DBA1/J mice (8-10 weeks old) were injected subcutaneously with collagen/CFA emulsion (50 µl/mouse; 100 µg/mouse collagen in CFA) using a 1 ml syringe with a 25 G needle. On day 20 a second injection with collagen/CFA emulsion was followed-up. Around day 28 mice were selected into three different treatment groups according to their clinical score with an average AI (arthritis index) of ~3-4 and IP treatment with PBS, 8 and 16 mg/kg (S)-mepazine (two injections per day, each either 4 mg/kg (resulting in a dose of 8 mg/kg/d) or 8 mg/kg (resulting in a dose of 16 mg/kg/d)) then started. The mice were scored according to the arthritis index with the following criteria: 0=no visible effects of arthritis; 1=edema and/or erythema of 1 digit; 2=edema and/or erythema of 2 digits; 3=edema and/or erythema of more than 2 digits; 4=severe arthritis of entire paw and digits. The index is calculated by addition of individual paw scores to a maximum AI of 16.

At the end of the study mice were euthanized and paws were collected for a histopathological analysis. Inflammation was scored with the following criteria: 0=normal; 1=minimal infiltration of inflammatory cells in synovium and periarticular tissue of affected joints; 2=mild infiltration, restricted to affected joints; 3=moderate infiltration with moderate edema, if paws, restricted to affected joints; 4=marked infiltration affecting most areas with marked edema; 5=severe diffuse infiltration with severe edema. Pannus: 0=normal; 1=minimal infiltration of pannus in cartilage and subchondral bone; 2=mild infiltration with marginal zone destruction of hard tissue in affected joints; 3=moderate infiltration with moderate hard tissue destruction in affected joints; 4=marked infiltration with marked destruction of joint architecture, most joints; 5=severe infiltration associated with total or near total destruction of joint architecture, affects all joints. Cartilage damage: 0=normal; 1=minimal to mild loss of toluidine blue staining with no obvious chondrocyte loss or collagen disruption in affected joints; 2=mild loss of toluidine blue staining with focal mild (superficial) chondrocyte loss and/or collagen disruption in affected joints; 3=moderate loss of toluidine blue staining with multifocal moderate (depth to middle zone) chondrocyte loss and/or collagen disruption in affected joints; 4=marked loss of toluidine blue staining with multifocal marked (depth to deep zone) chondrocyte loss and/or collagen disruption in most joints; 5=severe diffuse loss of toluidine blue staining with multifocal severe (depth to tide mark) chondrocyte loss and/or collagen disruption in all joints. Bone resorption 0=normal; 1=minimal, small areas of resorption, not readily apparent on low magnification, rare osteoclasts in affected joints; 2=mild, more numerous areas of, not readily apparent on low magnification, osteoclasts more numerous in affected joints; 3=moderate, obvious resorption of medullary trabecular and cortical bone without full thickness defects in cortex, loss of some medullary trabeculae, lesion apparent on low magnification, osteoclasts more numerous in affected joints; 4=marked, Full thickness defects in cortical bone, often with distortion of profile of remaining cortical surface, marked loss of medullary bone, numerous osteoclasts, affects most joints; 5=severe, Full thickness defects in cortical bone and destruction of joint architecture of all joints.

Example 1—Synthesis of Mepazine Enantiomers (R)- and (S)-mepazine were prepared from commercially available (R)- and (S)-carbamates 1, respectively. The preparation of (S)-mepazine is illustrated in Scheme 1. LiAlH$_4$ mediated reduction of the N-Boc protecting group of (S)-1 affords the N-methylpiperidine intermediate (S)-2. Formation of the tosylate followed by alkylation with the anion of phenothiazine affords (S)-mepazine, (S)-4. The enantiomeric purity of the enantiomers was confirmed by chiral HPLC analysis.

Scheme 1

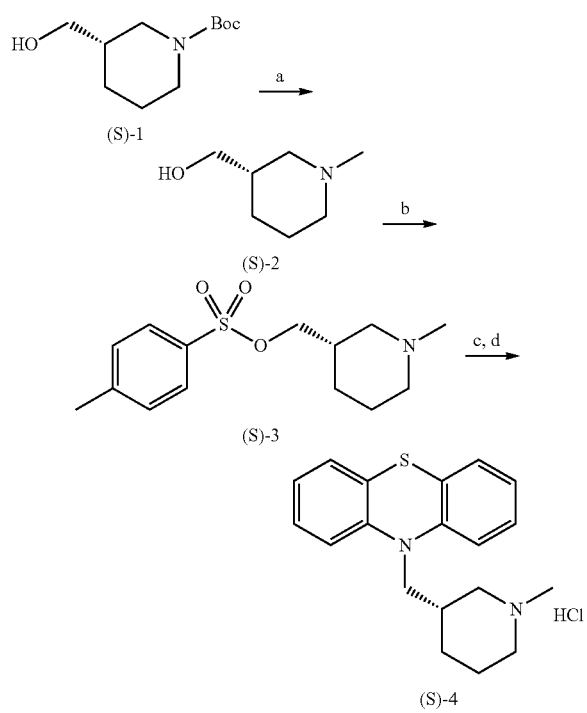

Reagents and conditions:
a) LiAlH$_4$, THF, 0° C. to RT, 95%;
b) 4-toluenesulfonyl chloride, 4-dimethylaminopyridine, CH$_2$Cl$_2$, 0° C. to RT, 85%;
c) phenothiazine, NaH, DMF then (S)-3;
d) ethanol, 1M aq. HCl, 49% (2 steps).

In an analogous manner, (R)-mepazine was prepared from carbamate (R)-1 (Scheme 2).

Scheme 2

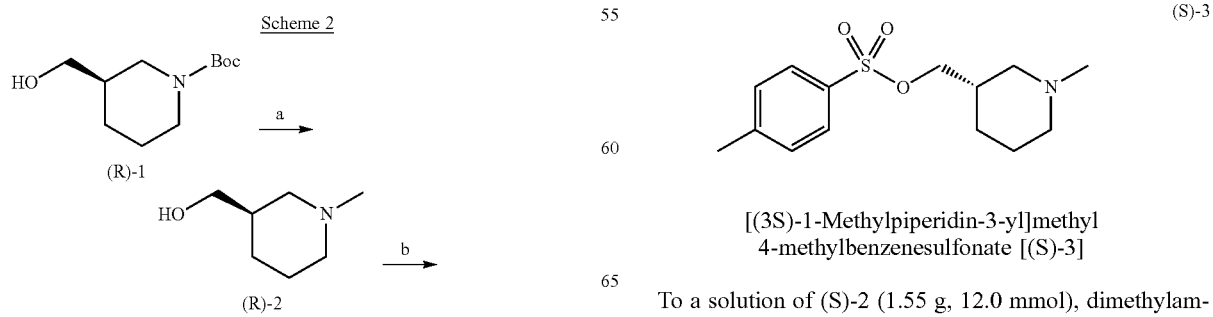

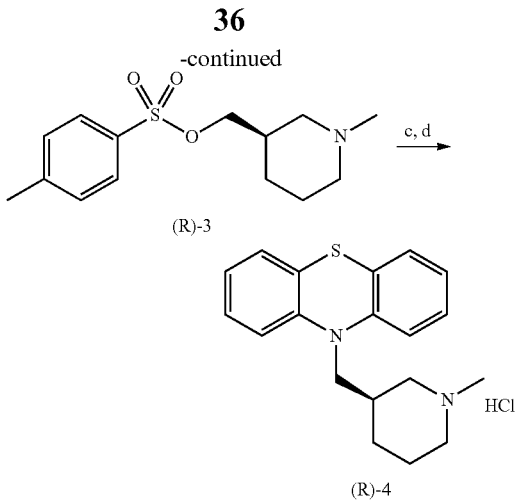

Reagents and conditions:
a) LiAlH$_4$, THF, 0° C. to RT, 67%;
b) 4-toluenesulfonyl chloride, 4-dimethylaminopyridine, CH$_2$Cl$_2$, 0° C. to RT, 75%;
c) phenothiazine, NaH, DMF then (R)-3;
d) ethanol, 1M aq. HCl, 28% (2 steps).

Synthesis of (S)-Mepazine

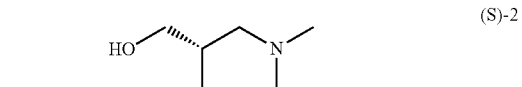

[(3S)-1-Methylpiperidin-3-yl]methanol [(S)-2]

To a solution of tert-butyl(3S)-3-(hydroxymethyl)piperidine-1-carboxylate, (S)-1 (5.0 g, 23.0 mmol) in THF (300 mL) at 0° C. was added 2.0 M lithium aluminum hydride in THF (17.4 mL, 34.8 mmol) and the reaction stirred for 20 hours while gradually warming to room temperature. The reaction was cooled to 0° C. and then water, 1.0 M sodium hydroxide and water were added (Fieser, "Reagents for Organic Synthesis", Wiley (1967)). This mixture was stirred overnight at room temperature and then filtered through a pad of Celite. Concentration of the filtrate afforded (S)-2 (3.0 g, 95%) as a colorless oil that was used without further purification.
$^1$H NMR (300 MHz, CDCl$_3$) δ (ppm)=1.04-1.14 (m, 1H), 1.55-1.84 (m, 3H), 1.91-1.95 (m, 1H), 2.03-2.09 (m, 1H), 2.26 (s, 3H), 2.61-2.64 (m, 1H), 2.78-2.82 (m, 1H), 3.51-3.66 (m, 2H), 3.74-3.78 (m, 1H). MS (ESI+) for C$_7$H$_{15}$NO m/z 130 (M+H)$^+$.

[(3S)-1-Methylpiperidin-3-yl]methyl 4-methylbenzenesulfonate [(S)-3]

To a solution of (S)-2 (1.55 g, 12.0 mmol), dimethylaminopyridine (73 mg, 0.60 mmol) and triethylamine (3.34 mL, 24.0 mmol) in DCM (80 mL) at 0° C. was added p-toluenesulfonyl chloride (2.52 g, 13.2 mmol) and the reaction stirred for 18 hours while gradually warming to room temperature. The mixture was diluted with 200 mL of DCM and washed three times with saturated sodium bicarbonate, once with water and once with brine. The organics were dried over sodium sulfate, filtered and concentrated under reduced pressure to afford (S)-3 (2.9 g, 85%) as a yellow oil that was used without further purification.

$^1$H NMR (300 MHz, CDCl$_3$) δ (ppm) 0.93-1.05 (m, 1H), 1.51-1.74 (m, 4H), 1.87-2.03 (m, 2H), 2.23 (s, 3H), 2.47 (s, 3H), 2.67-2.78 (m, 1H), 3.46-3.56 (m, 1H), 3.85-3.96 (m, 2H), 7.32-7.40 (m, 2H), 7.78-7.82 (m, 2H).

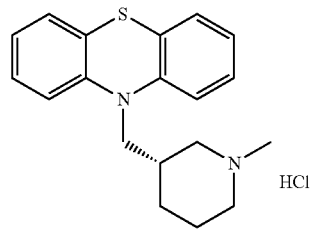

(S)-4

(S)-Mepazine Hydrochloride [(S)-4]

Sodium hydride (60% in mineral oil, 680 mg, 17.0 mmol) was added to a solution of phenothiazine (1.12 g, 5.64 mmol) in DMF (35 mL) and stirred for 30 minutes. Tosylate (S)-3 was then added as a solution in DMF (5 mL) and the reaction warmed to 50° C. and stirred for 18 hours. The reaction was quenched by the addition of 5 mL saturated ammonium chloride before transferring to a separatory funnel, diluting with 50 mL of ethyl acetate and washing three times with saturated sodium bicarbonate, once with water and once with brine. The organics were dried over sodium sulfate, filtered and concentrated under reduced pressure. The residue was purified by reverse phase chromatography (CombiFlash) using a gradient of 0-50% acetonitrile (containing 0.07% TFA) in water (containing 0.1% TFA). Like fractions were combined, neutralized with saturated sodium bicarbonate and extracted with ethyl acetate. The organic layer was dried over sodium sulfate, filtered and concentrated under reduced pressure. The residue (a colorless oil) was then dissolved in ethanol and 1M HCl, concentrated three times from ethanol and twice from ethyl acetate to afford (S)-4 (960 mg, 49% yield) as a light purple solid.

Chiral HPLC retention time: 7.32 min. $^1$H NMR (300 MHz, MeOD) δ (ppm)=1.25-1.36 (m, 1H), 1.62-1.77 (m, 1H), 1.97-2.13 (m, 2H), 2.40-2.50 (m, 1H), 2.73-2.92 (m, 2H), 2.81 (s, 3H), 3.40-3.49 (m, 1H), 3.56-3.65 (m, 1H), 3.86-3.94 (m, 1H), 4.05-4.13 (m, 1H), 6.97-7.02 (m, 2H), 7.06-7.09 (m, 2H), 7.19-7.27 (m, 4H); MS (ESI+) for C19H22N2S m/z 311 (M+H)$^+$.

(S)-Mepazine provided a single peak by Chiral HPLC under conditions in which the individual enantiomers are resolved. No racemization on standing or in solution was observed.

Synthesis of (R)-Mepazine

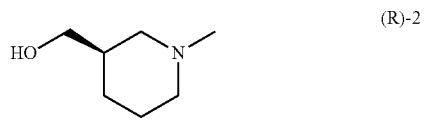

(R)-2

[(3R)-1-Methylpiperidin-3-yl]methanol [(R)-2)]

To a solution of tert-butyl(3R)-3-(hydroxymethyl)piperidine-1-carboxylate, (R)-1 (500 mg, 2.32 mmol) in THF (10 mL) at 0° C. was added 2.0 M lithium aluminum hydride in THF (1.39 mL, 2.79 mmol) and the reaction stirred for 20 hours while gradually warming to room temperature. The reaction was cooled to 0° C. and then water, 1.0 M sodium hydroxide and water were added. This mixture was stirred for 2.5 hours at room temperature and then filtered through a pad of Celite before concentrating the filtrate under reduced pressure to afford (R)-2 (200 mg, 67%) as a colorless oil that was used without further purification.

$^1$H NMR (300 MHz, CDCl$_3$) δ (ppm)=1.05-1.15 (m, 1H), 1.55-1.82 (m, 3H), 1.91-1.96 (m, 1H), 2.04-2.10 (m, 1H), 2.27 (s, 3H), 2.61-2.65 (m, 1H), 2.78-2.82 (m, 1H), 3.51-3.66 (m, 2H), 3.74-3.78 (m, 1H). MS (ESI+) for C$_7$H$_{15}$NO m/z 130 (M+H)$^+$.

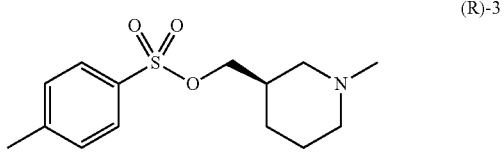

(R)-3

[(3R)-1-Methylpiperidin-3-yl]methyl 4-methylbenzenesulfonate [(R)-3]

To a solution of (R)-2 (200 mg, 1.55 mmol), dimethylaminopyridine (9 mg, 0.077 mmol) and triethylamine (0.432 mL, 3.10 mmol) in DCM (10 mL) at 0° C. was added p-toluenesulfonyl chloride (325 mg, 1.70 mmol) and the reaction stirred for 18 hours while gradually warming to room temperature. The reaction was diluted with 20 mL of DCM and washed three times with saturated sodium bicarbonate, once with water and once with brine. The organics were dried over sodium sulfate, filtered and concentrated under reduced pressure to afford (R)-3 (366 mg, 75%) of a yellow oil that was used without further purification.

$^1$H NMR (300 MHz, CDCl$_3$) δ (ppm)=0.94-1.08 (m, 1H), 1.54-1.77 (m, 4H), 1.88-2.03 (m, 2H), 2.24 (s, 3H), 2.47 (s, 3H), 2.68-2.78 (m, 1H), 3.49-3.57 (m, 1H), 3.86-3.97 (m, 2H), 7.32-7.39 (m, 2H), 7.78-7.82 (m, 2H).

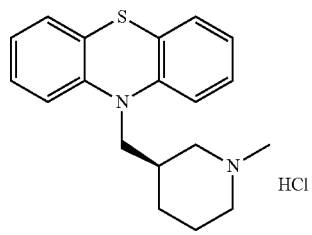

(R)-Mepazine Hydrochloride [(R)-4]

Sodium hydride (60% in mineral oil, 48 mg, 1.20 mmol) was added to a solution of phenothiazine (80 mg, 0.40 mmol) in DMF (3 mL) and stirred for 30 minutes. Tosylate (R)-3 was then added as a solution in DMF (1 mL) and the reaction warmed to 50° C. and stirred for 18 hours. The reaction was quenched by the addition of 1 mL saturated ammonium chloride and diluted with 50 mL of ethyl acetate. The organic layer was washed three times with saturated sodium bicarbonate, once with water and once with brine. The organics were dried over sodium sulfate, filtered and concentrated under reduced pressure. The residue was purified by reverse phase chromatography (CombiFlash) using a gradient of 0-50% acetonitrile (containing 0.07% TFA) in water (containing 0.1% TFA). Like fractions were combined, neutralized with saturated sodium bicarbonate and extracted with ethyl acetate. The organic layer was dried over sodium sulfate, filtered and concentrated under reduced pressure. This colorless oil was then dissolved in ethanol and 1M HCl, concentrated three times from ethanol and twice from ethyl acetate to afford (R)-4 (40 mg, 28% yield) as a white solid.

Chiral HPLC retention time: 7.50 min. $^1$H NMR (300 MHz, MeOD) δ (ppm)=1.25-1.36 (m, 1H), 1.62-1.77 (m, 1H), 1.97-2.13 (m, 2H), 2.40-2.50 (m, 1H), 2.73-2.92 (m, 2H), 2.81 (s, 3H), 3.40-3.49 (m, 1H), 3.56-3.65 (m, 1H), 3.86-3.94 (m, 1H), 4.05-4.13 (m, 1H), 6.97-7.02 (m, 2H), 7.06-7.09 (m, 2H), 7.19-7.27 (m, 4H). MS (ESI+) for C$_{19}$H$_{22}$N$_2$S m/z 311 (M+H)$^+$.

Example 2—Synthesis of Thioridazine Enantiomers

Enantiomerically pure thioridazine isomers 7f and 7s were prepared as reported (Scheme 3 and Choi et al., *Med. Chem. Lett.* 14, 4379-4382 (2004)). N-Demethylation of racemic thioridazine followed by reaction with (−)-menthyl chloroformate provided, after chromatographic separation, diastereomers 6f and 6s. The absolute configuration of the diastereomers was not established. Reduction of individual diastereomers with LiAlH$_4$ provided 7f and 7s, respectively. The enantiomeric purity of the isomers was confirmed by chiral HPLC analysis.

Scheme 3

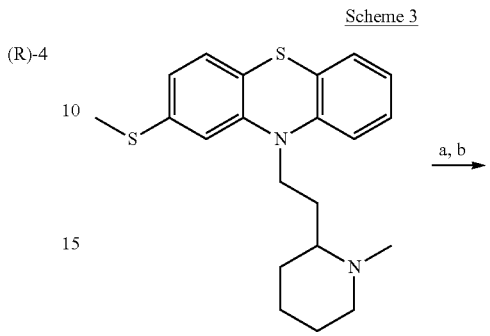

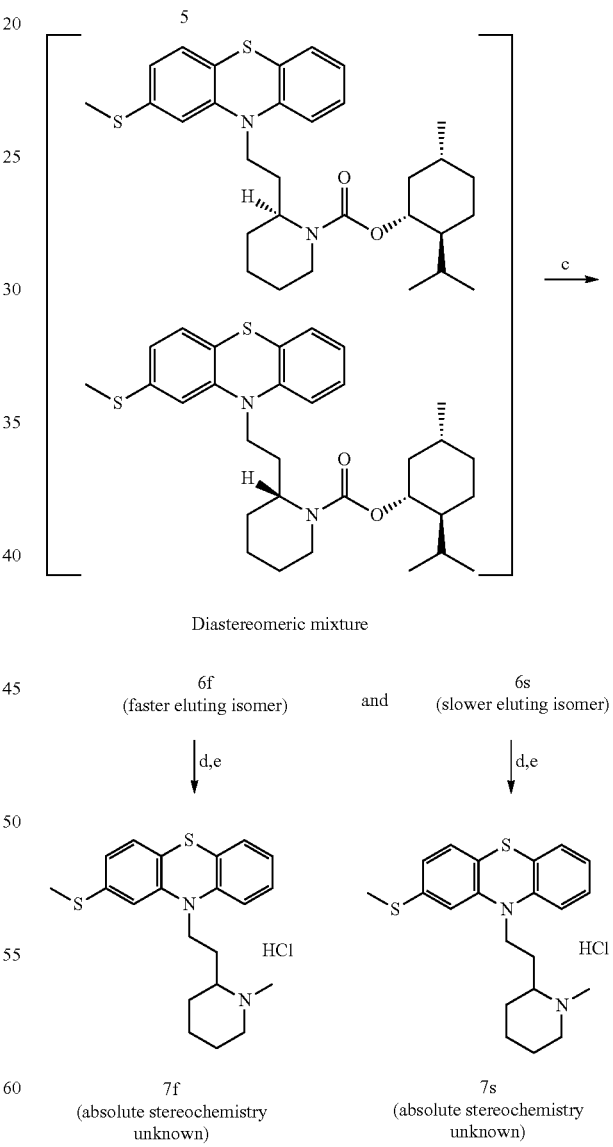

6f (faster eluting isomer) and 6s (slower eluting isomer)

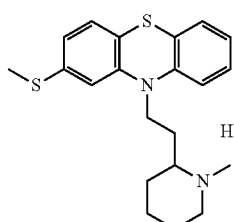

7f (absolute stereochemistry unknown)

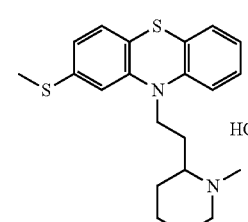

7s (absolute stereochemistry unknown)

Reagents and conditions: a) 1-chloroethyl chloroformate, 1,2-dichloroethane, reflux, then MeOH, reflux; b) (-)-menthyl chloroformate, i-Pr$_2$EtN, CH$_2$Cl$_2$, RT; c: silica gel chromatography, 6f 19% (2 steps, faster eluting diastereomer) and 6s 21% (2 steps, slower eluting isomer); d) LiAlH$_4$, THF, 50° C., 7f 26%; 7s 19%; e) ethanol, 1 M aq. HCl, quant.

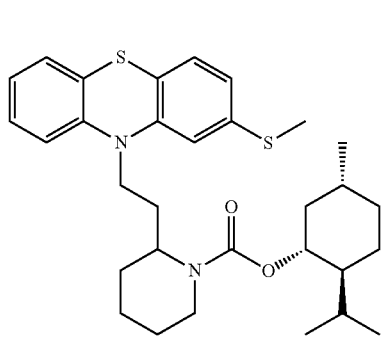

6f and 6s (1R,2S,5R)-2-Isopropyl-5-methylcyclohexyl 2-{2-[2-(methylthio)-10H-phenothiazin-10-yl]ethyl}-piperidine-1-carboxylate (6f and 6s)

To a solution of thioridazine (800 mg, 2.16 mmol) in 1,2-dichloroethane at 0° C. was added 1-chloroethyl chloroformate (0.256 mL, 2.37 mmol) and the reaction was warmed to reflux for 3 hours. The reaction was cooled to room temperature and then concentrated under reduced pressure. To the residue was added methanol (20 mL, 500 mmol) and the resulting solution heated at reflux for 18 hours. The mixture was concentrated under reduced pressure and the residue dissolved in 20 mL of DCM. To this solution was added DIEA (0.827 mL, 4.75 mmol) followed by (R)-(−)-menthyl chloroformate (0.555 mL, 2.59 mmol) before stirring 18 hours at room temperature. At that time the contents of the flask were transferred to a separatory funnel, diluted with DCM (50 mL) and washed three times with saturated sodium bicarbonate, once with water and once with brine. The combined organic layers were dried over sodium sulfate, filtered and concentrated under reduced pressure. The residue that remained was purified by flash chromatography using 0-10% ethyl acetate in hexane to afford 6f (faster eluting diastereomer, 225 mg, 19%) as a colorless oil and 6s (slower eluting isomer, 238 mg, 21%) as a light yellow oil.

6f: HPLC retention time: 7.02 min; $^1$H NMR (400 MHz, CDCl$_3$): δ (ppm)=0.83-0.85 (m, 3H), 0.90-0.96 (m, 5H), 0.98-1.06 (m, 1H), 1.08-1.16 (m, 1H), 1.36-1.44 (m, 2H), 1.51-1.72 (m, 13H), 1.90-2.07 (m, 3H), 2.17-2.28 (m, 1H), 2.48 (s, 3H), 2.83-2.90 (m, 1H)), 3.78-3.89 (m, 2H), 4.04-4.12 (m, 1H), 4.47-4.53 (m, 1H), 4.58-4.65 (m, 1H), 6.79-6.79 (m, 1H), 6.84-6.88 (m, 2H), 6.93-6.97 (m, 1H), 7.08-7.09 (m, 1H), 7.16-7.20 (m, 2H); MS (ESI+) for C$_{31}$H$_{42}$N$_2$O$_2$S$_2$ m/z 539 (M+H)$^+$.

6s: HPLC retention time: 6.76 min.; $^1$H NMR (400 MHz, CDCl$_3$): δ (ppm)=0.78-0.83 (m, 3H), 0.90-0.94 (m, 5H), 1.02-1.11 (m, 1H), 1.37-1.68 (m, 14H), 1.86-1.95 (m, 2H), 2.19-2.29 (m, 1H), 2.48 (s, 3H), 2.82-2.90 (m, 1H), 3.80-3.92 (m, 2H), 4.08-4.17 (m, 1H), 4.47-4.58 (m, 2H), 6.79-6.80 (m, 1H), 6.84-6.89 (m, 2H), 6.92-6.97 (m, 1H), 7.07-7.11 (m, 1H), 7.15-7.19 (m, 2H); MS (ESI+) for C$_{31}$H$_{42}$N$_2$O$_2$S$_2$ m/z 539 (M+H)$^+$.

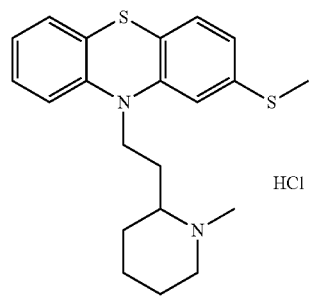

7f

10-[2-(1-Methylpiperidin-2-yl)ethyl]-2-(methylthio)-10H-phenothiazine hydrochloride (7f)

To a solution of 6f (200 mg, 0.371 mmol) in THF (10 mL, 100 mmol) at 0° C. was added 2.0 M lithium aluminum hydride in THF (0.278 mL, 0.557 mmol). The reaction was warmed to room temperature and then heated at 50° C. for 18 hours. At that time the reaction was cooled to 0° C. and water, 1M sodium hydroxide and water were added. The mixture was stirred overnight and then filtered through a pad of Celite. The filtrate was concentrated under reduced pressure and the remaining residue purified by flash chromatography using 0-5% methanol in DCM to afford the desired product (36 mg, 26%) as a colorless oil. This oil was dissolved in ethanol and 1M HCl, concentrated under reduced pressure and then concentrated from ethyl acetate twice to afford 7f as a white solid in quantitative yield.

Chiral HPLC retention time: 12.85 min. $^1$H NMR (400 MHz, MeOD) δ (ppm)=1.48-1.58 (m, 2H), 1.70-2.10 (m, 6H), 2.51 (s, 3H), 2.69 (s, 3H), 2.97-3.17 (m, 2H), 3.37-3.47 (m, 1H), 4.05-4.19 (m, 2H), 6.92-6.96 (m, 2H), 7.00-7.04 (m, 1H), 7.08-7.10 (m, 1H), 7.12-7.14 (m, 1H), 7.20-7.23 (m, 1H), 7.25-7.29 (m, 1H); MS (ESI+) for C$_{21}$H$_{26}$N$_2$S$_2$ m/z 371 (M+H)$^+$.

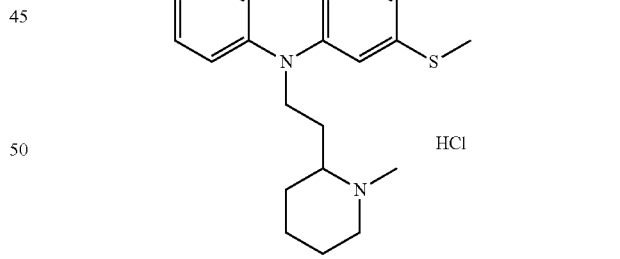

7s

10-[2-(1-Methylpiperidin-2-yl)ethyl]-2-(methylthio)-10H-phenothiazine hydrochloride (7s)

In an analogous manner, 6s (220 mg, 0.408 mmol) provided 7s (29 mg, 19%) as a colorless oil. This oil was dissolved in ethanol and 1M HCl, concentrated under reduced pressure and then concentrated from ethyl acetate twice to afford 7s as a white solid in quantitative yield.

Chiral HPLC retention time: 12.11 mm. $^1$H NMR (400 MHz, MeOD) δ (ppm)=1.48-1.58 (m, 2H), 1.70-2.10 (m, 6H), 2.51 (s, 3H), 2.69 (s, 3H), 2.97-3.17 (m, 2H), 3.37-3.47

(m, 1H), 4.05-4.19 (m, 2H), 6.92-6.96 (m, 2H), 7.00-7.04 (m, 1H), 7.08-7.10 (m, 1H), 7.12-7.14 (m, 1H). 7.20-7.23 (m, 1H), 7.25-7.29 (m, 1H); MS (ESI+) for $C_{21}H_{26}N_2S_2$ m/z 371 (M+H)$^+$.

Example 3—Crystal Structure of MALT1 in Complex with Thioridazine

The X-ray data collection and refinement statistics are shown in Table 1.

TABLE 1

Data collection and refinement statistics.

| Data collection | thioridazine MALT1$_{Casp-Ig3}$ | anomalous thioridazine MALT1$_{Casp-Ig3}$ |
|---|---|---|
| PDB entry code | 4I1R | — |
| Space group | C2 | C2 |
| Unit Cell dimensions | | |
| a, b, c (Å) | 94.8, 70.6, 57.5 | 94.9, 70.7, 57.5 |
| α, β, γ (°) | 90.0, 93.6, 90.0 | 90.0, 93.6, 90.0 |
| Resolution range (Å) | 47.32-2.70 | 47.34-2.84 |
| Total number of reflections | 32428 (5189) | 48550 (7373) |
| Unique reflections | 10533 (1667) | 17169 (2688) |
| Completeness (%) | 98.6 (97.8) | 97.4 (94.7) |
| Multiplicity | 3.08 (3.11) | 2.83 (2.74) |
| R$_{merge}$[a] | 3.8 (61.2) | 5.4 (51.5) |
| I/σI | 17.69 (1.75) | 11.79 (1.80) |
| Refinement | | |
| R$_{work}$[b]/R$_{free}$[c] | 0.2005/0.2492 | |
| Wilson B-factor (Å$^2$) | 88.5 | |
| Number of water molecules | 26 | |
| RMSD from ideal values | | |
| Bond lengths (Å) | 0.013 | |
| Bond angles (°) | 1.26 | |
| Ramachandran plot no. of residues/% | | |
| Most favoured regions | 328 (95.35%) | |
| Allowed regions | 15 (4.36%) | |
| Residues in disallowed regions | 1 (0.29%) | |

Values in parentheses are for highest-resolution shell.
[a]Rmerge = (Σ|I − <I>|)/ΣI, where I is the observed intensity and <I> is the average intensity obtained after multiple observations of symmetry related reflections.
[b]R$_{work}$ = (Σ||Fo| − |Fc||)/ΣFo, where Fo are observed and Fc calculated structure factors.
[c]Rfree uses 5% randomly chosen reflections The crystal structure of ligand free dimeric human MALT1$_{Casp-Ig3}$ in complex with the phenothiazine derivative thioridazine revealed that the phenothiazine derivative bound in a pocket located on the opposite site relative to the caspase active site, in the interface between the caspase domain and the Ig3 domain connecting helix α1$_{Ig3}$ of MALT1 (FIG. 1a). This allosteric binding site, far apart from the catalytic center well explains the fact that certain phenothiazine derivatives act as non-competitive, reversible inhibitors (Nagel et al., Cancer cell, 2012, 22, 825-837). Superposition of the enzymatic active MALT1$_{Casp-Ig3}$ construct bound to the hex-LRSR-AOMK peptide with the thioridazine bound structure indicated that binding of the compound between helices α1$_{Ig3}$ and αC prevented the conformational change into an active enzyme, the so called second activation step of MALT1 (FIG. 1 and Wiesmann et al., J. Mol. Biol. (2012), 419, 4-21). Besides ligand induced active site loop rearrangements three major shifts of helices αC, αD and the β sheets 3A and 3B are essential to achieve the enzymatic proficient protease conformation (FIG. 1b). The movement of helices αC and continuative αD was hampered by the sandwiched thioridazine and subsequently β sheets 3A and 3B could not perform their pivotal shift (FIG. 1b). A detailed analysis of the inhibitor binding site showed that the tricyclic ring system of thioridazine was bound in a hydrophobic pocket composed of residues A394, F398, L401 in helix αC and L346, V344 and V381 in β sheets 1 and 2, respectively. The orientation of the 2-methylsulfanylphenothiazine ring was proven by collecting a dataset at a wavelength of 1.9 Å to detect the anomalous signal of sulfur. Upon inhibitor binding, the side chain of residue tryptophan W580 on helix α1$_{Ig3}$ was flipped out of the hydrophobic groove into a solvent exposed environment which led to a substantial displacement of helix α1$_{Ig3}$ (FIG. 1c). Probably triggered by rotation of this domain-connecting helix the entire Ig3 domain became more flexible and shifted at the tip of the domain up to 7 Å compared to the peptide bound MALT1 structure (FIG. 1a).

Example 4—Tryptophan Fluorescence Quenching Assay

Figure 2:
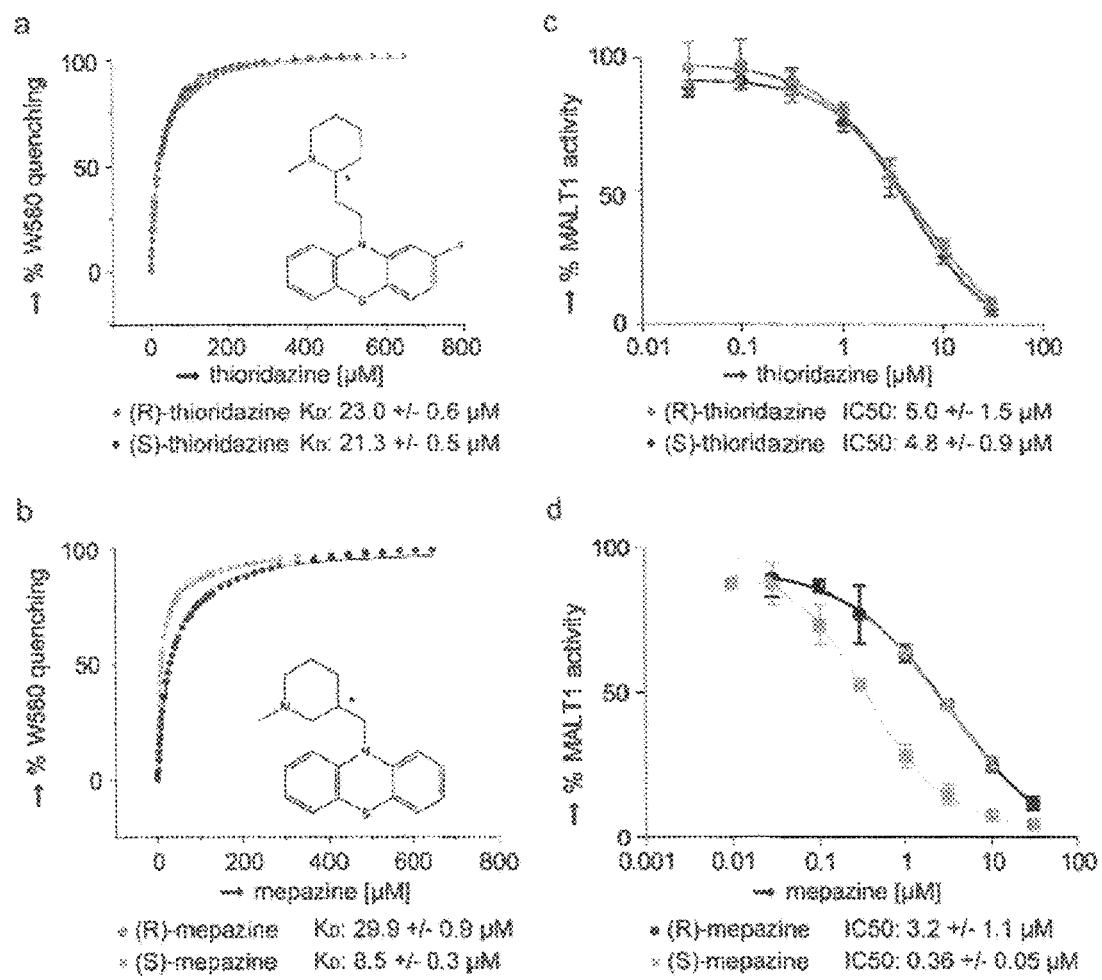
FIG. 2: Mepazine enantiomers have different MALT1 inhibitory potential. (a) and (b) Tryptophan quenching assay with the single enantiomers of thioridazine ((R): ●; (S): ♦) and mepazine ((R): ●, (S): ■), respectively. (c) and (d) MALT1 cleavage assay with wt GST-MALT1$_{325-760}$ after incubation with either the (R)- or (S)-enantiomer of mepazine ((R): ●, (S): ■) or thioridazine ((R): ●; (S): ♦). Curves show the mean of at least three independent experiments with SD indicated.

To verify the mechanism of inhibition of MALT1 by certain phenothiazine derivatives such as mepazine and thioridazine a tryptophan fluorescence quenching assay was developed. For this assay advantage was taken from the fact that W580 is the only tryptophan residue in the MALT1$_{Casp-Ig3}$ construct and is in close proximity to the bound tricyclic moiety of the phenothiazine derivatives. The tryptophan fluorescence of monomeric MALT1$_{Casp-Ig3}$ was recorded with increasing amounts of thioridazine (FIG. 2a). The titration was continued until saturation of quenching was observed.

Example 5—MALT1 Inhibitory Potential

A detailed inspection of the inhibitor electron density map suggests that solely the (S)-enantiomer of thioridazine is bound in the crystal structure (FIG. 1). To analyze the influence of chirality on the binding affinity and inhibitory potential, the individual enantiomers of mepazine and thioridazine were prepared as described above and analyzed accordingly.

Whereas (R)- and (S)-thioridazine showed equivalent binding affinity ($K_D$: (R)-thioridazine: 23.0±0.6 µM; (S)-thioridazine: 21.3±0.5 µM; cf. FIG. 2a) and IC50 values ((R)-thioridazine: 5.0±1.5 µM; (S)-thioridazine: 4.8±0.9 µM; cf. FIG. 2c), (S)-mepazine exhibited a significant higher binding affinity ($K_D$: 8.5±0.3 µM; cf. FIG. 2b) and an about 9 fold increased inhibitory potential (IC50: 0.36±0.05 µM; cf. FIG. 2d) compared to (R)-mepazine ($K_D$: 29.9±0.9 µM; IC50: 3.2±1.1 µM; cf. FIGS. 2b and d).

Figure 3:
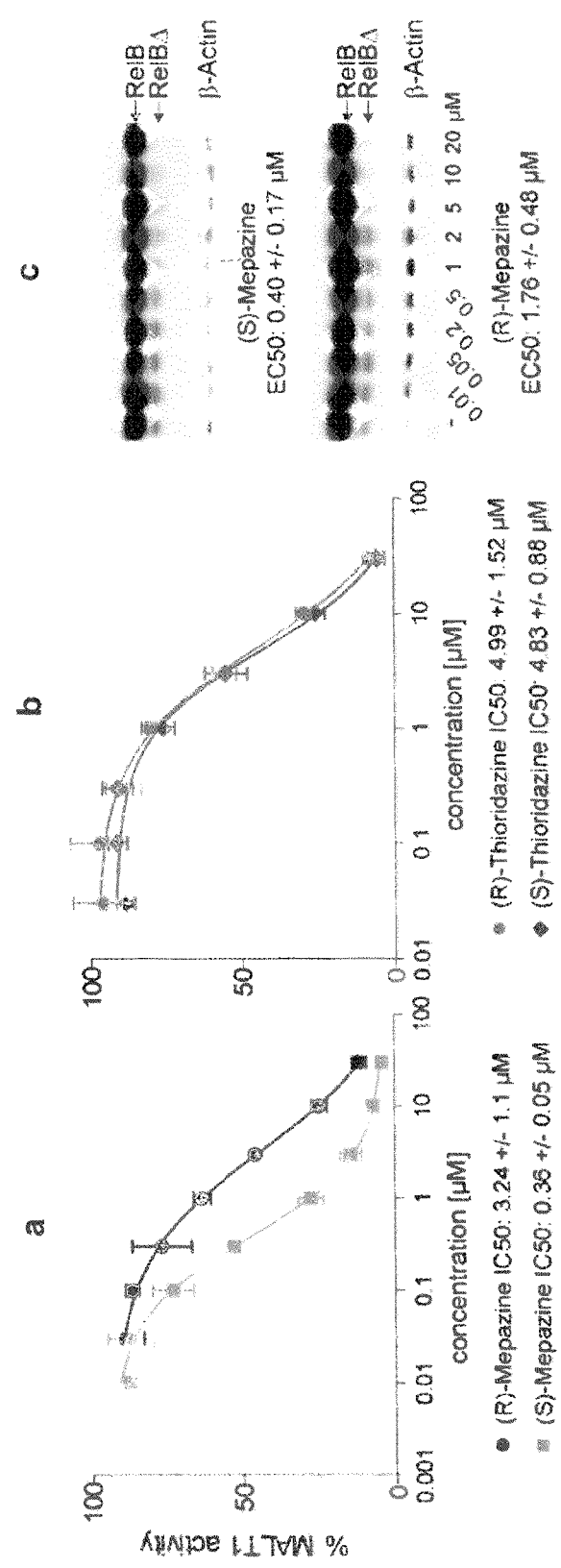
FIG. 3: (S)-Mepazine with stronger inhibitory impact on MALT1. (a) and (b) Fluorogenic MALT1 cleavage assay after incubation with one of the (S)- and (R)-enantiomers of mepazine ((R): ●, (S): ■) and thioridazine ((R): ●; (S): ♦). Curves show the mean of at least three independent experiments and error bars represent SD. (c) Detection of the cellular MALT1-derived RelB cleavage. Treatment of the ABC-DLBCL cell-line HBL1 (2.5×10$^5$/ml) with increasing amounts of (S)-mepazine (upper panel) and (R)-mepazine (lower panel). The Western Blot is representative for at least three experiments and EC50 values were calculated with PRISM 5 (GraphPad).

To further analyze the influence of chirality on the binding affinity and inhibitory potential of the individual enantiomers of mepazine and thioridazine, these enantiomers were analyzed using a fluorogenic MALT1 cleavage assay and the cellular RelB cleavage via Western Blot detection (Nagel et al., Cancer cell, 2012, 22, 825-837). Whereas (R)- and (S)-thioridazine showed equivalent IC50 values on recombinant MALT1 ((R)-thioridazine: 4.99±1.52 µM; (S)-thioridazine: 4.83±0.88 µM; cf. FIG. 3b), (S)-mepazine exhibited a significant increased inhibitory potential (IC50: 0.36±0.05 µM) compared to (R)-mepazine (IC50: 3.24±1.1 µM; FIG. 3a). An incubation of the ABC-DLBCL HBL1 cell line with both mepazine enantiomers showed a dose-dependent rescue of MALT1-derived RelB cleavage (FIG. 3c). Comparable to their effects on recombinant MALT1 the enantiomers had a different impact on cellular MALT1 with (S)- mepazine having a much lower EC50 (0.40±0.17 μM) compared to the (R)-enantiomer (1.76±0.48 μM).

Example 6—In Vivo Potential of (S)-Mepazine

Figure 4:
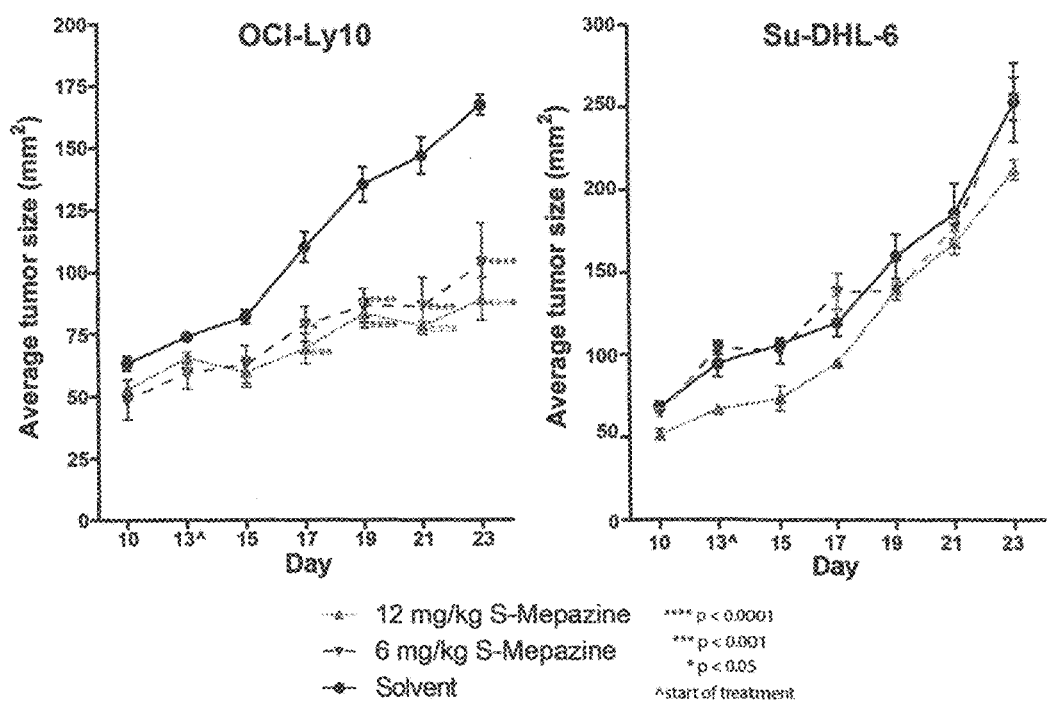
FIG. 4: (S)-Mepazine selectively reduced the growth of the MALT1-dependent ABC DLBCL tumor. The ABC DLBCL cell-line OCI-Ly10 and the GCB DLBCL cell-line Su-DHL-6 were injected into immune compromised mice (NSG) where they grow to a solid tumor. Treatment with 2 doses of (S)-mepazine (6 mg/kg: ▼; 12 mg/kg: ▲; each once daily) led to a selective growth reduction of the OCI-Ly10 tumor, whereas the GCB DLBCL control tumor was not affected.

To determine the in vivo potential of (S)-mepazine the compound was tested in different pre-clinical murine models. In the DLBCL xenograft model NSG mice were subcutaneously injected with the MALT1-dependent ABC DLBCL cell line OCI-Ly10 and the MALT1-independent GCB DLBCL cell-line Su-DHL6 in opposing flanks of individual mice. After 13 days of tumor growth the mice were treated with PBS and two doses of (S)-mepazine. Both doses led to a selective growth reduction of the ABC DLBCL tumor, whereas the GCB DLBCL control tumor was not affected, demonstrating a specific and selective anti-tumor potency of (S)-mepazine (FIG. 4).

Figure 5:
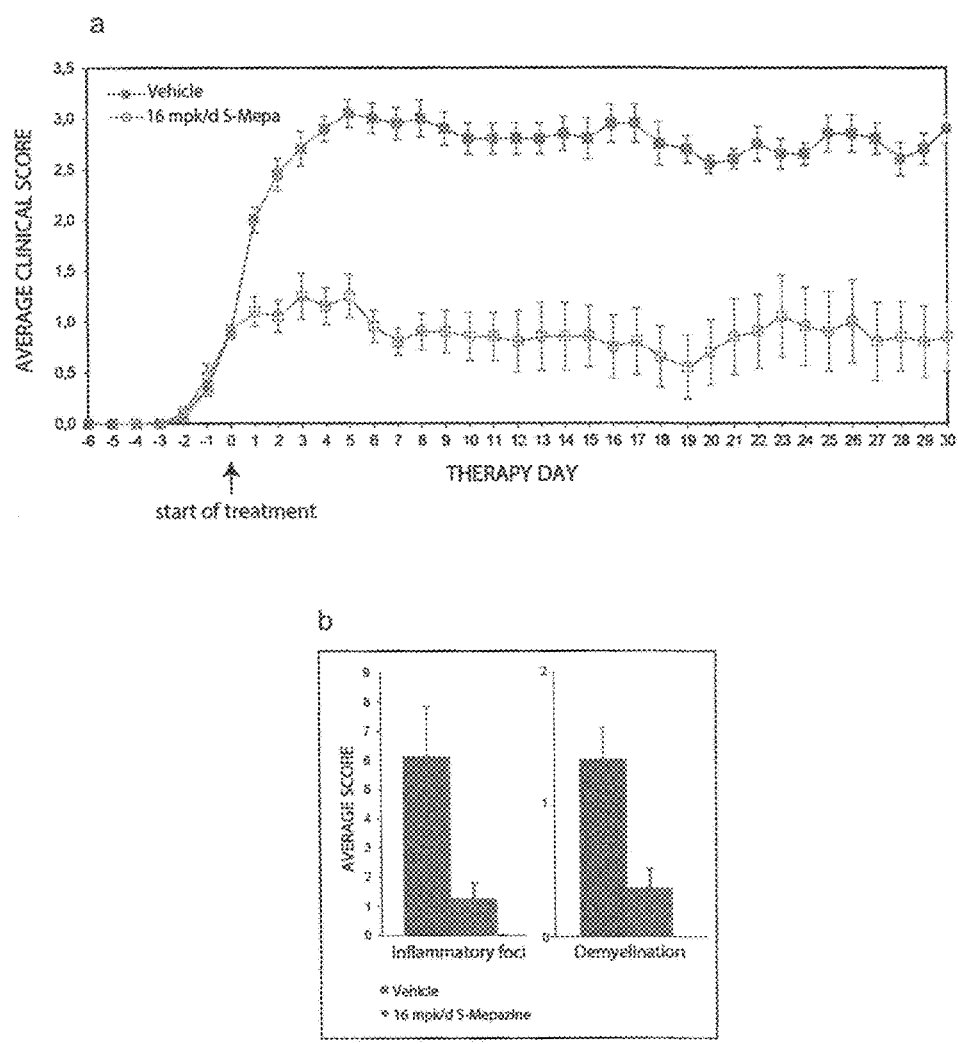
FIG. 5: (S)-Mepazine led to a reduction of EAE severity and weight loss. (a) Treatment of EAE mice with (S)-mepazine (intraperitoneal (IP) injection of 8 mg/kg twice daily) led to a reduction of EAE severity. Significance (p-value) was calculated in relation to vehicle treated control by two-way ANOVA (p<0.01 to p<0.0001 from day 2-30). (b) (S)-Mepazine treatment resulted in an inhibition of inflammatory foci formation and demyelination in the spinal cord. (c) (S)-Mepazine treatment reduced EAE induced weight loss of the mice.
Figure 5:
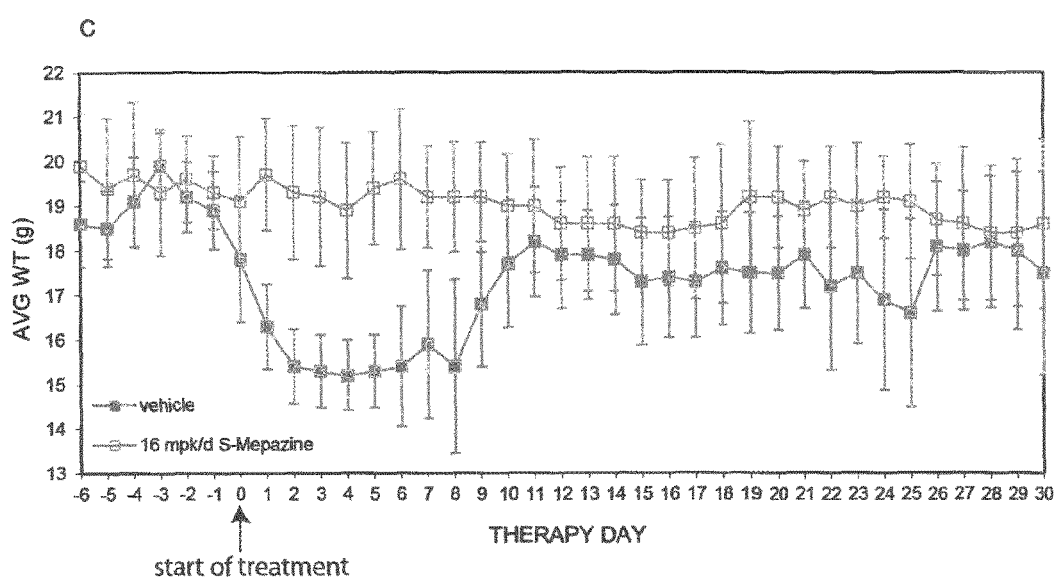

To further profile (S)-mepazine for a possible application in immune disorders we tested the compound in two murine models, EAE (experimental allergic encephalomyelitis) and CIA (collagen-induced arthritis), which are models for multiple sclerosis and rheumatoid arthritis, respectively. In the EAE model the mice were first immunized with $MOG_{35-55}$ peptides and the treatment with (S)-mepazine (16 mg/kg) started after they developed a clinical disease score of around 1. (S)-Mepazine treatment resulted in a reduction of EAE severity (FIG. 5a). This result was mirrored by the histopathological data where inflammatory foci formation and demyelination of neurons was also reduced (FIG. 5b). Furthermore, (S)-mepazine treatment reduced EAE induced weight loss of the mice (FIG. 5c).

Figure 6:
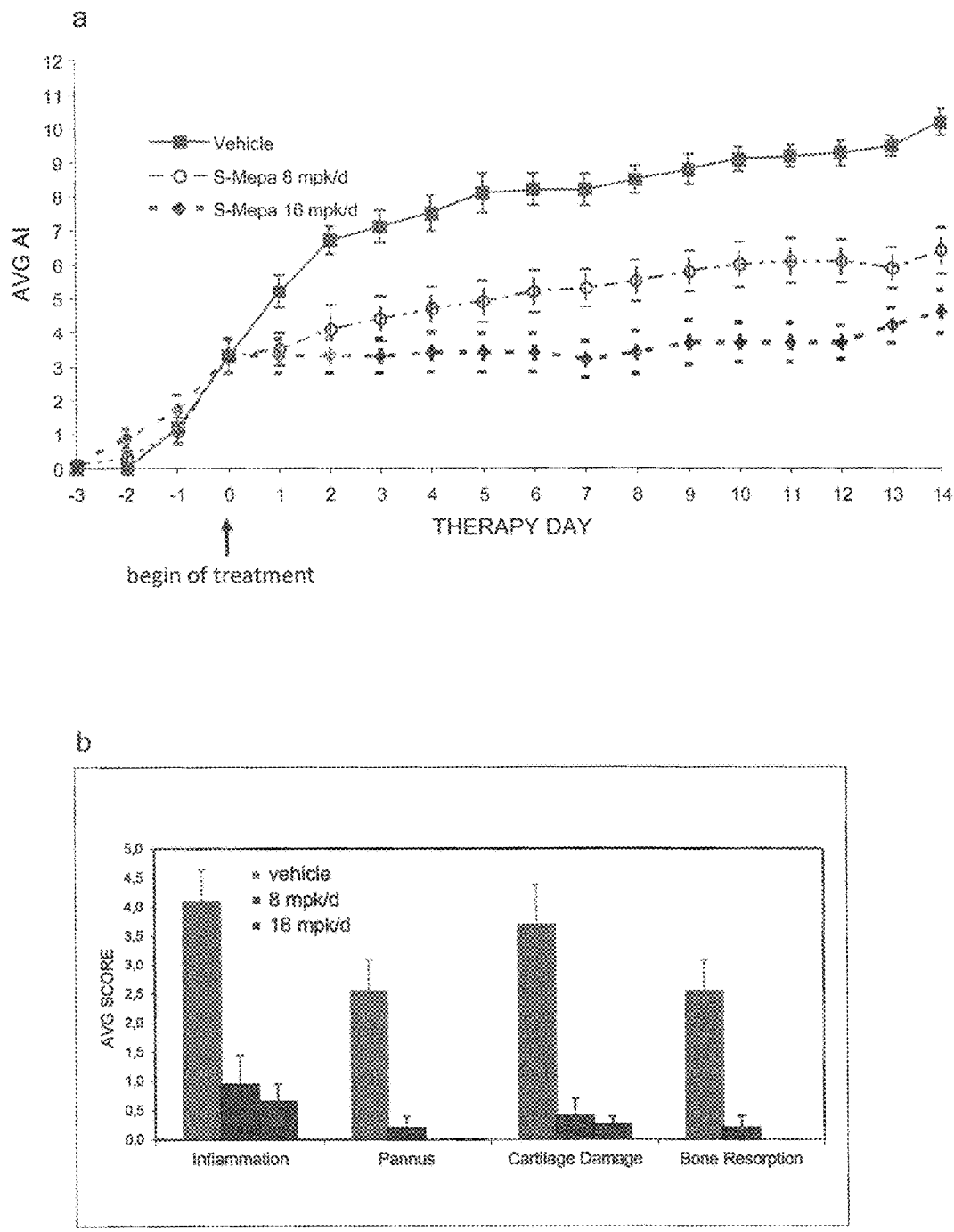
FIG. 6: (S)-Mepazine led to a reduction of CIA severity. (a) Treatment of CIA mice with (S)-mepazine (IP injection of 4 or 8 mg/kg twice daily resulting in a daily dose of 8 or 16 mg/kg) led to a dose-dependent reduction of disease severity. Significance (p-value) was calculated in relation to vehicle treated control by two-way ANOVA, ranging from day 2-14 from p<0.01 to p<0.0001 for the 8 mg/kg and p<0.0001 for the 16 mg/kg treatment. (b) (S)-mepazine treatment resulted in a decrease of CIA-related inflammation, pannus formation, cartilage damage and bone resorption.

A similar result was observed in the CIA model where the treatment of the mice was started with a clinical score of 3-4. Here, (S)-mepazine also significantly reduced the severity of the disease (FIG. 6a). The improved phenotype of the diseased mice also correlated with a strong reduction of CIA-related inflammation, pannus formation, cartilage damage and bone resorption (FIG. 6b).

The invention claimed is:

1. A compound selected from the group consisting of 10-{[(3S)-1-methylpiperidin-3-yl]methyl}-10H-phenothiazine (the S-enantiomer of mepazine) and solvates, salts, isotopically labeled forms and combinations thereof.

2. The compound of claim 1 which is the hydrochloride, acetate, or tartrate salt of (S)-mepazine.

3. A pharmaceutical composition comprising the compound of claim 1 and a pharmaceutically acceptable excipient.

4. A method of inhibiting mucosa-associated lymphoid tissue lymphoma translocation protein 1 (MALT1) paracaspase, the method comprising contacting a paracaspase with a compound of claim 1.

5. A method for treating a disease or disorder which is A treatable by an inhibitor of MALT1 paracaspase, the method comprising administering to a subject a compound of claim 1.

6. A process for preparing the compound of claim 1, comprising reacting phenothiazine with a piperidine derivative of the following formula (3)

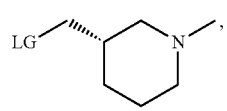

(3)

wherein LG is a leaving group.

7. The process of claim 6, further comprising converting a tertiary amine of the following formula (2)

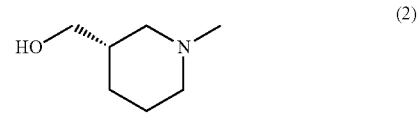

(2)

into the piperidine derivative of formula (3).

8. The process of claim 7, further comprising converting a carbamate of the following formula (1)

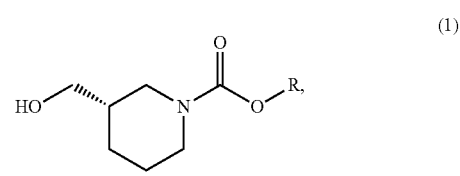

(1)

wherein R is an optionally substituted alkyl, cycloalkyl, heterocyclyl, aryl, or heteroaryl group, into the tertiary amine of formula (2).

9. The process of claim 8, wherein converting the carbamate of formula (1) into the tertiary amine of formula (2) is conducted in presence of a reducing agent.

10. The process of claim 7, wherein reacting phenothiazine with the piperidine derivative of formula (3) and/or converting the tertiary amine of formula (2) into the piperidine derivative of formula (3) is conducted in presence of a chemical base.

11. The process of claim 6, wherein LG is selected from the group consisting of Br, Cl, mesylate, triflate, and tosylate.

12. A process for preparing a tertiary amine of the following formula (2)

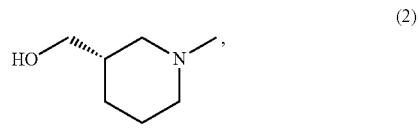

(2)

comprising reacting a carbamate of the following formula (1)

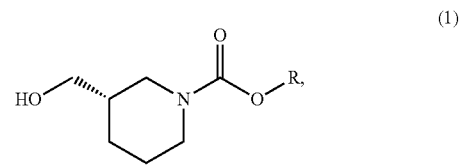

(1)

wherein R is an optionally substituted alkyl, cycloalkyl, heterocyclyl, aryl, or heteroaryl group, with a reducing agent.

13. The process of claim 12, wherein the reducing agent is $LiAlH_4$.

14. The process of claim 9, wherein the reducing agent is $LiAlH_4$.

15. The method of claim 5, wherein the disease or disorder is (i) cancer, or (ii) a MALT1 paracaspase-dependent immune disease.

16. The method of claim 15, wherein the cancer is a lymphoma.

17. The method of claim 16, wherein the lymphoma is mucosa-associated lymphoid tissue (MALT) lymphoma or diffuse large B-cell lymphoma (DLBCL), such as activated B-cell subtype of diffuse-large B cell lymphoma (ABC-DLBCL).

18. The method of claim 1, wherein the MALT1 paracaspase-dependent immune disease is an allergic inflammation or an autoimmune disease.

19. A pharmaceutical composition comprising the compound of claim 2 and a pharmaceutically acceptable excipient.

* * * * *